(12) United States Patent
Palombi et al.

(10) Patent No.: US 12,297,161 B2
(45) Date of Patent: May 13, 2025

(54) PROCESS FOR MAKING SARECYCLINE HYDROCHLORIDE

(71) Applicants: PARATEK PHARMACEUTICALS, INC., Boston, MA (US); ALMIRALL, LLC, Exton, PA (US)

(72) Inventors: Giovanni Palombi, Monza (IT); Eugenio Castelli, Arlate (IT); Giuseppe Motta, Rescaldina (IT); Meinrad Brenner, Steg (CH); Ruiliang Lu, Guangzhou (CN); Shaozhi Huang, Foshan (CN); William Paul Armstrong, Carrickfergus (GB); Gajanan Joshi, South Plainfield, NJ (US); Farzaneh Seyedi, Boston, MA (US); Sean Johnston, Boston, MA (US)

(73) Assignee: ALMIRALL, LLC, Malvern, PA (US)

( * ) Notice: Subject to any disclaimer, the term of this patent is extended or adjusted under 35 U.S.C. 154(b) by 880 days.

(21) Appl. No.: 17/043,017

(22) PCT Filed: Apr. 5, 2019

(86) PCT No.: PCT/CN2019/081620
§ 371 (c)(1),
(2) Date: Sep. 29, 2020

(87) PCT Pub. No.: WO2019/192614
PCT Pub. Date: Oct. 10, 2019

(65) Prior Publication Data
US 2021/0017123 A1 Jan. 21, 2021

Related U.S. Application Data

(60) Provisional application No. 62/657,201, filed on Apr. 13, 2018, provisional application No. 62/654,070, filed on Apr. 6, 2018.

(51) Int. Cl.
*C07C 231/12* (2006.01)
*C07C 237/26* (2006.01)

(52) U.S. Cl.
CPC .......... *C07C 231/12* (2013.01); *C07C 237/26* (2013.01); *C07C 2603/46* (2017.05)

(58) Field of Classification Search
CPC .. C07C 231/12; C07C 237/26; C07C 2603/46
See application file for complete search history.

(56) References Cited

U.S. PATENT DOCUMENTS

2009/0156842 A1* 6/2009 Seyedi ................. C07C 231/12
552/205
2010/0305072 A1 12/2010 Kim et al.
2013/0012480 A1 1/2013 Coulter et al.

FOREIGN PATENT DOCUMENTS

WO WO 2004/038001 A2 5/2004

OTHER PUBLICATIONS

International Search Report for International Application No. PCT/CN2019/081620, mailed Jun. 28, 2019.
(Continued)

*Primary Examiner* — Clinton A Brooks
*Assistant Examiner* — Kyle Nottingham
(74) *Attorney, Agent, or Firm* — Finnegan, Henderson, Farabow, Garrett & Dunner LLP

(57) ABSTRACT

The described invention relates to sarecycline, related compounds, intermediates and salts thereof and processes for preparing the same.

10 Claims, 1 Drawing Sheet

(56) References Cited

OTHER PUBLICATIONS

Written Opinion of the International Searching Authority for International Application No. PCT/CN2019/081620, mailed Jun. 28, 2019.

* cited by examiner

PROCESS FOR MAKING SARECYCLINE HYDROCHLORIDE

This application is a national stage filing under 35 U.S.C. § 371 of International Application No. PCT/CN2019/081620, filed on Apr. 5, 2019, which claims priority of U.S. Provisional Application No. 62/654,070, filed Apr. 6, 2018, and U.S. Provisional Application No. 62/657,201, filed Apr. 13, 2018. The contents of these applications are each incorporated herein by reference.

FIELD OF THE INVENTION

The described invention relates to sarecycline, related compounds, intermediates and salts thereof and processes for preparing the same.

BACKGROUND OF THE INVENTION

Tetracyclines

Tetracycline compounds, or tetracyclines, are "broad spectrum" antibiotics and have been widely used for therapeutic purposes. The parent compound chlortetracycline (tradename Aureomycin) was first isolated from *Streptomyces aureofaciens* in 1947 (Duggar B M. Aureomycin: a product of the continuing search for new antibiotics. Ann NY Acad Sci 51:177-181, 1948). Soon after, other natural tetracyclines were isolated, including tetracycline, for which the family of molecules is named. Since then, the modifications of naturally occurring tetracyclines and the synthesis of novel compounds within the tetracycline family have generated many compounds (Griffin M O et al. Am J Physiol Cell Physiol. 2010 September; 299 (3): C539-C548). Examples of these tetracycline compounds include chlortetracycline, doxycycline, minocycline, oxytetracycline, demeclocycline, methacycline, sancycline, chelocardin, rolitetracycline, lymecycline, apicycline; clomocycline, guamecycline, meglucycline, mepylcycline, penimepicycline, pipacycline, etamocycline, penimocycline.

Chemical Properties of Tetracyclines

Tetracyclines are all composed of a four-ring core to which are attached various side groups as illustrated by the chemical structure of tetracycline below.

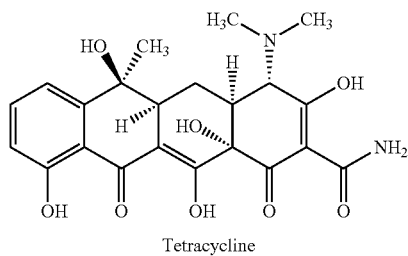

Tetracycline

The dimethylamino group at the C4 carbon on the upper half of the molecule has been shown to be necessary for antimicrobial activity (Griffin M O et al. Am J Physiol Cell Physiol. 2010 September; 299 (3): C539-C548). 4-De-dimethylamino tetracyclines, also called chemically modified tetracyclines (CMTs), lack in vivo antimicrobial activity due to the inability of the molecule to adapt a zwitterionic form necessary for activity (McNamara T F, Golub L M, D'Angelo G, Ramamurthy N S. The synthesis and characterization of non-antimicrobial chemically-modified tetracycline (CMT) (Abstract). J Dent Res 65: IADR no. 515, 1986). However, CMTs do retain the ability to bind other nonmicrobial targets, such as matrix metalloproteinases (MMPs), facilitating their use in the treatment of other disease processes (Golub L M, McNamara T F, D'Angelo G, Greenwald R A, Ramamurthy N S. A non-antibacterial chemically-modified tetracycline inhibits mammalian collagenase activity. J Dent Res 66:1310-1314, 1987). The oxygen-rich lower half of the molecule is critical for binding to both prokaryotic and eukaryotic targets, and interference with this region reduces or eliminates the effectiveness of the drug (Golub L M, Ramamurthy N S, McNamara T F, Greenwald R A, Rifkin B R. Tetracyclines inhibit connective tissue breakdown: new therapeutic implications for an old family of drugs. Crit Rev Oral Biol Med 2:297-321, 1991). This region is relevant as a site for metal ion chelation (Griffin M O et al. Am J Physiol Cell Physiol. 2010 September; 299 (3): C539-C548). Binding of tetracyclines to proteins, including TetR, may be greatly enhanced when the tetracycline is complexed with divalent metal ions such as $Ca^{2+}$ or $Mg^{2+}$ (Takahashi M, Altschmied L, Hillen W. Kinetic and equilibrium characterization of the Tet repressor-tetracycline complex by fluorescence measurements. Evidence for divalent metal ion requirement and energy transfer. J Mol Biol 187:341-348, 1986). In addition, binding to the bacterial ribosome involves binding to RNA-bound $Mg^{2+}$ (Goldman R A, Hasan T, Hall C C, Strycharz W A, Cooperman B S. Photoincorporation of tetracycline into *Escherichia coli* ribosomes. Identification of the major proteins photolabeled by native tetracycline and tetracycline photoproducts and implications for the inhibitory action of tetracycline on protein synthesis. Biochemistry 22:359-368, 1983).

Uses of Tetracyclines

Tetracyclines have been found to be highly effective pharmacologically against rickettsiae, a number of gram-positive and gram-negative bacteria and the agents responsible for lymphogranuloma venereum, inclusion conjunctivitis, and psittacosis. Examples of pharmaceutically active tetracycline analogue compositions may be found in U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. Some tetracyclines may also be used to treat inflammatory skin disorders, including dermatitis, psoriasis, pyoderma gangrenosum, acne, and rosacea.

Mechanism of Action of Tetracyclines

Tetracyclines exert their antibiotic effect primarily by binding to the bacterial ribosome and halting protein synthesis (Hash J H, Wishnick M, Miller P A. On the mode of action of the tetracycline antibiotics in *Staphylococcus aureus*. J Biol Chem 239:2070-2078, 1964). Bacterial ribosomes have a high-affinity binding site located on the 30S subunit and multiple low-affinity sites on both the 30S and 50S subunits (Tritton T R. Ribosome-tetracycline interactions. Biochemistry 16:4133-4138, 1977). Upon binding the ribosome, the tetracyclines allosterically inhibit binding of the amino acyl-tRNA at the acceptor site (A-site), and protein synthesis ceases (Semenkov YuP, Makarov E M, Makhno V I, Kirillov S V. Kinetic aspects of tetracycline action on the acceptor (A) site of *Escherichia coli* ribosomes. FEBS Lett 144:125-129, 1982).

Bacterial Resistance to Tetracyclines

The use of tetracyclines has declined in recent decades due to the emergence of resistant bacterial strains. The primary mechanism of resistance is mediated by increased drug efflux out of the cell by a family of Tet proteins located on the cytoplasmic surface of the cell membrane (Levy S B, McMurry L. Detection of an inducible membrane protein associated with R-factor-mediated tetracycline resistance. Biochem Biophys Res Commun 56:1060-1068, 1974; Yamaguchi A, Udagawa T, Sawai T. Transport of divalent cations with tetracycline as mediated by the transposon Tn10-encoded tetracycline resistance protein. J Biol Chem 265:4809-4813, 1990). After the widespread use of tetracyclines for both major and minor illnesses and diseases led to resistance to these antibiotics, substituted tetracycline compounds were developed to treat bacterial infections, inflammation, neoplasms, and other conditions. Examples of these tetracycline compounds include: chlortetracycline, doxycycline, minocycline, oxytetracycline, demeclocycline, methacycline, sancycline, chelocardin, rolitetracycline, lymecycline, apicycline, clomocycline, guamecycline, meglucycline, mepylcycline, penimepicycline, pipacycline, etamocycline, and penimocycline. For example, substituted tetracycline compounds have been disclosed in WO 2008/079339 and WO 2008/079363.

Sarecycline

Sarecycline ((4S, 4aS, 5aR, 12aS)-4-dimethylamino-3, 10, 12, 12A-tetrahydroxy-7-[methoxy (methyl) amino)-methyl] acid amide) is a once-daily, tetracycline-class antibiotic with a narrow spectrum of antibacterial activity, including more limited activity against aerobic Gram-negative gastrointestinal (GI) organisms than minocycline and doxycycline (Leyden J J et al. June 2017 Volume 76, Issue 6, Supplement 1, page AB113). Sarecycline also has demonstrated a narrow spectrum of activity targeting acne and rosacea specific pathogens (e.g., P. acnes and S. aureus). This activity may be due to a higher lipophilicity at physiologically relevant pH allowing better penetration into lipid-rich sebaceous follicular tissue. In addition, sarecycline has demonstrated anti-inflammatory activity. For example, sarecycline has been shown to reduce inflammatory lesions of moderate to severe acne vulgaris (See, e.g., Leyden J J et al. June 2017 Volume 76, Issue 6, Supplement 1, page AB113).

Presently, the process for synthesizing sarecycline (e.g., sarecycline hydrochloride) shown in FIG. 1 of U.S. Pat. No. 8,513,223 B2 and U.S. Pat. No. 9,255,068 B2 involves the following steps: (a) conversion of sancycline to 7-iodosancycline; (b) Palladium catalyzed coupling of 7-iodosancycline to form 7-substituted aldehyde intermediate (7-formylsancycline) (c) Reductive amination of 7-formylsancycline in presence of appropriately substituted hydroxylamine to give crude sarecycline hydrochloride salt followed by either column chromatographic purification or extractive isolation, work up and crystallization to obtain corresponding sarecycline free base, which in turn (d) is converted back again to the sarecycline hydrochloride salt. This process is often time consuming due to multiple preparative high-performance liquid chromatography (HPLC) purifications that may be required to obtain the desired high purity of sarecycline free base or HCl salt, sometimes resulting in gel formation of intermediates (especially at the second intermediate if appropriate solvent is not used). In addition, this process proceeds through reactions which are not driven to completion (e.g., in steps 2 and 3) and ultimately results in (i) a low yield of intermediates; (ii) assay and purity of intermediates; and (iii) final sarecycline hydrochloride salt due to carryover of impurities from step to step and loss of products in multiple purification operations. Also, the above process is not scalable, efficient and robust for production of multi-hundreds of kilogram quantities of sarecycline HCl that is often required for commercial use.

Thus, a need exists for new and improved methods for preparing tetracyclines such as sarecycline (e.g., sarecycline hydrochloride) at a large scale without performing the aforementioned tedious process. The described invention provides a new and improved method for preparing sarecycline, related compounds, intermediates and salts thereof (e.g., sarecycline hydrochloride) while eliminating the need for multiple preparative column chromatographic purifications at commercial scale with an improved efficiency. The described invention also highlights a process optimization that has resulted in (i) reaction completion; (ii) reduced formation and carryover of impurities, thus producing the desired intermediates; and (iii) a final product with yields, assay and purity required for commercial use. The described invention also eliminates several problems encountered during small scale-up manufacture of intermediates, such as gel formation; failed in-process controls; phase separation during isolation and work-up; and purging of undesired impurities thus producing a final product of the highest possible purity.

SUMMARY OF THE INVENTION

According to one aspect, the described invention provides a process for preparing sarecycline hydrochloride of Formula (I)

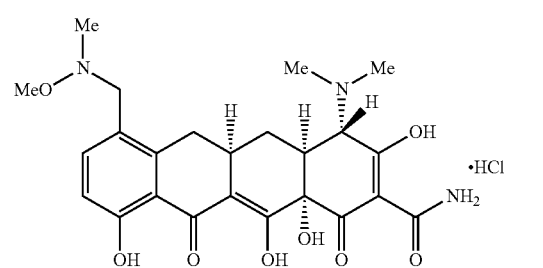

comprising (a) reacting (4S, 4aS, 5aR, 12aR)-4-(dimethylamino)-1, 10, 11, 12a-tetrahydroxy-3, 12-dioxo-4a, 5, 5a, 6-tetrahydro-4H-tetracene-2-carboxamide of Formula II

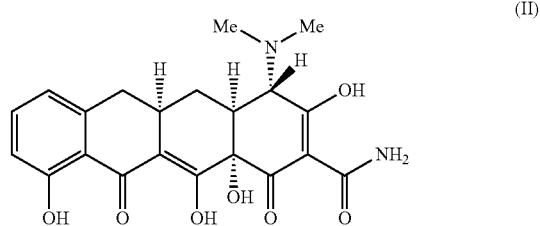 [SMILES: CN(C)[C@@H]1C(O)=C(C(N)=O)C(=O)[C@@]2(O)C(O)=C3C(=O)c4c(O)cccc4C[C@H]3C[C@@H]12]

with trifluoracetic acid (TFA) and N-iodosuccinimide (NIS) to form 7-iodosancycline trifluoroacetic acid salt of Formula III

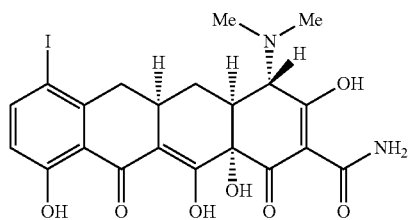

(b) reacting the 7-iodosancycline trifluoroacetic acid salt of Formula III with N-methyl pyrrolidone (NMP), triphenylphosphine (PPh₃), Bis-(Triphenyl Phosphine) palladium chloride catalyst (BTPP—PdCl₂), triethylsilane (Et₃SiH) and carbon monoxide (CO) to form 7-formylsancycline of Formula IV

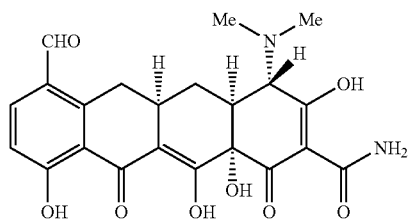

(c) reacting the 7-formylsancycline of Formula IV with dimethylhydroxylamine (DMHA) free base, oxalic acid, dimethylaminoborane (DMAB) and acetone to form sarecycline crude oxalate salt of Formula V

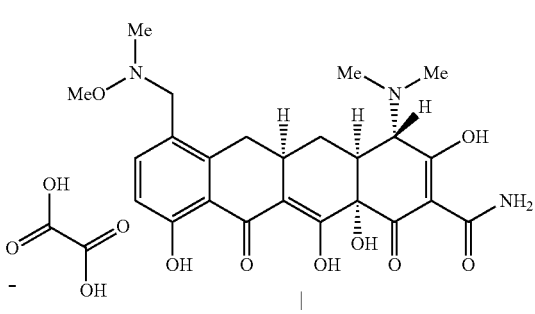

(d) reacting the sarecycline crude oxalate salt of Formula V with ammonium hydroxide (NH₃ (aq.)) or hydrochloric acid (HCl) to form sarecycline free base of Formula VI

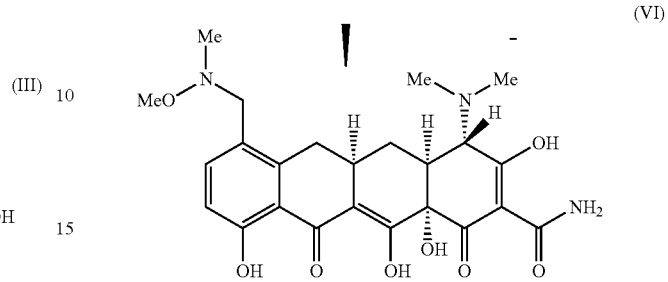

and (e) reacting the sarecycline free base of Formula VI with ethanolic hydrochloric acid solution to form the sarecycline hydrochloride of Formula I.

According to one embodiment, step (a) further comprises isopropanol; or tetrahydrofuran (THF); or isopropanol and tetrahydrofuran (THF). According to another embodiment, step (b) further comprises cellulose or SiO₂; or sodium carbonate (Na₂CO₃); or water; or sulfuric acid (H₂SO₄); or ethanol (EtOH); or a combination thereof. According to another embodiment, step (c) further comprises methanol (MeOH). According to another embodiment, step (d) further comprises cellulose or SiO₂; or dichloromethane (DCM); or water; or methanol (MeOH); or acetone; or a combination thereof. According to another embodiment, step (e) further comprises ethanol (EtOH); or water; or hydrochloric acid (HCl); or a combination thereof.

According to one embodiment, step (d) is repeated at least one time.

According to one embodiment, the process for preparing sarecycline hydrochloride of Formula (I) further comprises (d') reacting the sarecycline free base of Formula VI with trifluoroacetic acid (TFA); and tetrahydrofuran (THF) and repeating steps (d) and (c). According to another embodiment, step (d') further comprises water; or isopropanol; or water and isopropanol. According to another embodiment, steps (d') and (d) are repeated at least one time.

According to one embodiment, the sarecycline hydrochloride of Formula I comprises an impurity. According to another embodiment, the impurity is selected from the group consisting of sancycline, 9-sarecycline, 7-formylsancycline, 7, 9-sarecycline, 4R-sarecycline, 7-methoxyiminomethylsancycline and a combination thereof. According to another embodiment, the sancycline is about ≤1.0% (w/w %). According to another embodiment, the 9-sarecycline is about ≤1.0% (w/w %). According to another embodiment, the 7-formylsancycline about ≤1.0% (area %). According to another embodiment, the 7, 9-sarecycline is about ≤1.0% (w/w %). According to another embodiment, the 4R-sarecycline is about ≤3.0% (w/w %). According to another embodiment, the 7-methoxyiminomethylsancycline is about ≤1.0% (w/w %).

According to one embodiment, the sarecycline hydrochloride of Formula I comprises ≤1.5 to 6.0% (w/w %) of total impurities. According to another embodiment, the total impurities are selected from the group consisting of sancycline, 9-sarecycline, 7-formylsancycline, 7, 9-sarecycline, 4R-sarecycline, 7-methoxyiminomethylsancycline, and a combination thereof. According to another embodiment, the sancycline is about ≤1.0% (w/w %). According to another embodiment, the 9-sarecycline is about ≤1.0% (w/w %). According to another embodiment, the 7-formylsancycline about ≤1.0% (area %). According to another embodiment, the 7, 9-sarecycline is about ≤1.0% (w/w %). According to another embodiment, the 4R-sarecycline is about ≤3.0% (w/w %). According to another embodiment, the 7-methoxyiminomethylsancycline is about ≤1.0% (w/w %).

DETAILED DESCRIPTION OF THE INVENTION

Figure 1:
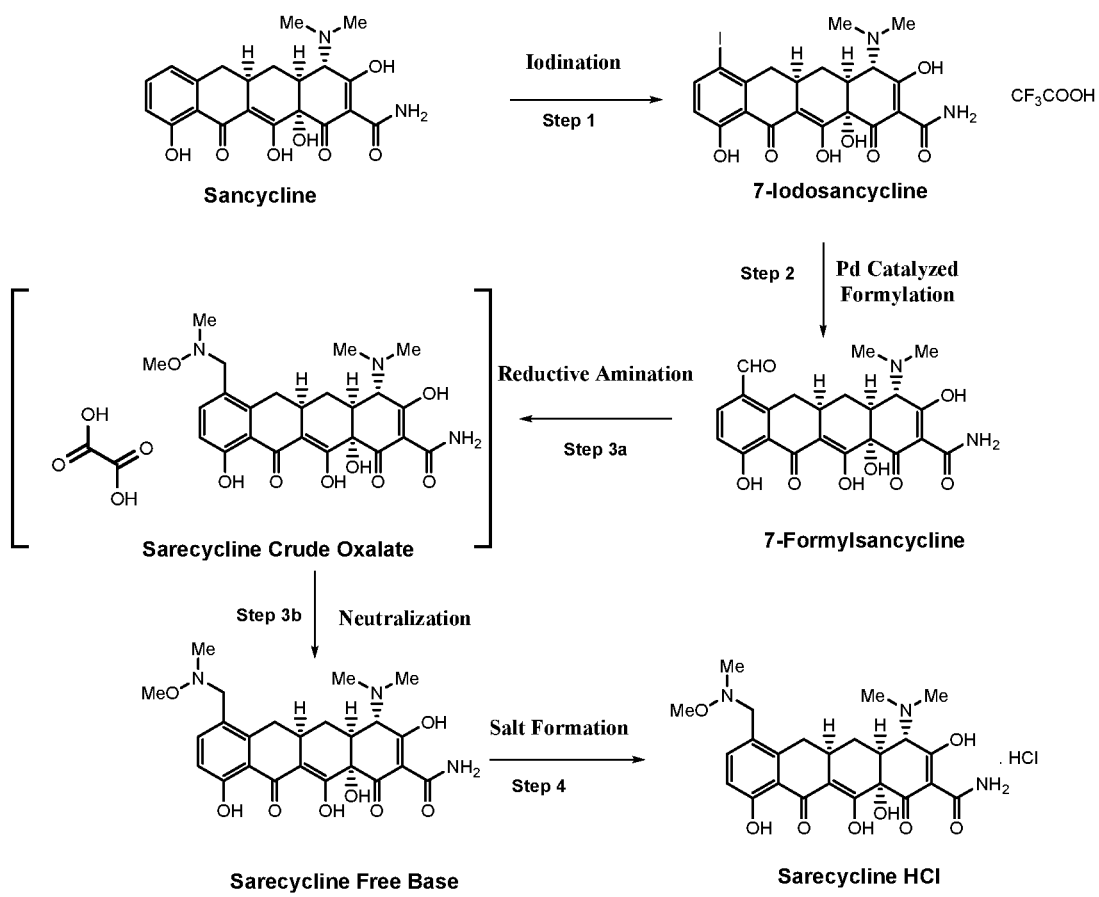
FIG. 1 shows a schematic of the sarecycline hydrochloride manufacturing process.

The present invention can be better understood from the following description of exemplary embodiments, taken in conjunction with the accompanying FIGURES and drawings. It should be apparent to those skilled in the art that the described embodiments of the present invention provided herein are merely exemplary and illustrative and not limiting.

Definitions

Various terms used throughout this specification shall have the definitions as set out herein.

The term "active" or "active ingredient" or "AI" or "active pharmaceutical ingredient" or "API" or "bulk active" as used herein, refers to an ingredient, component or constituent responsible for an intended therapeutic effect. Stated another way, a substance in a drug that is pharmaceutically active.

The term "assay" as used herein, refers to the purity of a substance. The lower the assay, the lower the purity of a substance, and conversely, the higher the assay, the higher the purity of a substance. By way of example, an assay of 100% means that a substance contains no impurities.

The term "batch" or "lot" as used interchangeably herein, refers to a defined quantity of starting material, packaging material or product processed in one process or series of processes so that it could be expected to be homogeneous.

The term "catalyst" as used herein, refers to a substance that increases the rate of a chemical reaction without itself undergoing any permanent chemical change.

The term "charge" and its various grammatical forms as used herein, means to add.

The term "crystal" as used herein, refers to a solid with an ordered internal arrangement of molecules, ions, or atoms.

The term "crystallization" as used herein, refers to the physical transformation (phase transition) of a liquid, solution, or gas to a crystal.

The term "drug substance" as used herein, refers to an active ingredient that is intended to furnish pharmacological activity or other direct effect in the diagnosis, cure, mitigation, treatment, or prevention of disease or to affect the structure or any function of the human body, but does not include intermediates used in the synthesis of the active ingredient.

The term "epimer" as used herein, refers to each of two isomers with different configurations or atoms around one of several asymmetric carbon atoms present.

The term "intermediate" as used herein, refers to a chemical compound synthesized from simpler compounds and usually intended to be used in later syntheses of more complex products. An intermediate is usually a short-lived chemical species formed in a reaction as an intermediate step between the starting material and the final product.

The terms "isolate" and "purify" and their various grammatical forms as used interchangeably herein, mean to separate a molecule, a material or a substance from another molecule, material or substance or other molecules, materials or substances, so that the molecule, material or substance is substantially or essentially free from components that normally accompany or interact with it, to an extent practical and appropriate for its intended use. A molecule, a material or a substance is substantially pure when it has been substantially separated from the substances with which it may be associated for example, during a manufacturing or a synthesis process. As used herein, the term "substantially pure" or "essentially pure" refers to purity of at least 75%, at least 80%, at least 85%, at least 90%, at least 95% or at least 99% pure as determined by an analytical method. Such methods include, but are not limited to, spectroscopy, mass spectroscopy, electrochemical analysis, thermal analysis, chromatography (e.g., high-performance liquid chromatography (HPLC)) and the like.

The term "isomer" as used herein, refers to each of two or more compounds with the same formula but a different arrangement of atoms in the molecule and different properties.

The term "Karl Fischer titration" or "KF" as used herein, refers to an analytical chemical method that uses coulometric or volumetric titration to determine trace amounts of water in a sample.

The term "Loss on Drying" or "LOD" as used herein, refers to a method used to determine the moisture content of a sample.

The term "mole" as used herein, refers to an International System of Units (SI) unit which measures the number of particles in a specific substance. One (1) mole is equal to $6.02 \times 10^{23}$ atoms or other elementary units such as molecules.

The term "pharmaceutically acceptable salt" as used herein, refers to any adduct between two or more chemical species that are capable of undergoing proton transfer. As such, the term "pharmaceutically acceptable salt" encompasses adducts in which complete proton transfer has occurred, adducts in which partial proton transfer has occurred (e.g., in which an equilibrium mixture of charged and uncharged species is formed), and/or adducts in which proton transfer has not occurred but the chemical species are associated e.g., by hydrogen bonding. It is understood that the term "pharmaceutically acceptable salt" also encompasses adducts in which close ion pairs are present. It will also be understood that the term "pharmaceutically acceptable salt" encompasses a continuum of adducts between those adducts in which complete proton transfer has occurred to form discrete ions and/or adducts in which two species are associated but proton transfer has not occurred, or has only partially occurred (See, e.g., Aitipamula et al. *Mol. Pharmaceutics*, 2007, 4 (3), pp 323-338). A given pharmaceutically acceptable salt can contain one or multiple adducts on this continuum.

Pharmaceutically acceptable salts include, but are not limited to, salts of acidic or basic groups. Pharmaceutically acceptable acid addition salts include, but are not limited to, hydrochloride, hydrobromide, hydroiodide, nitrate, mesylate, sulfate, bisulfate, phosphate, acid phosphate, isonicotinate, acetate, lactate, salicylate, citrate, tartrate, pantothenate, bitartrate, ascorbate, succinate, maleate gentisinate, fumarate, gluconate, glucaronate, saccharate, formate, benzoate, glutamate, methanesulfonate, ethanesulfonate, benzensulfonate, ptoluenesulfonate and pamoate (i.e., 1,1'-methylene-bis-(2-hydroxy-3-naphthoate)) salts. Suitable base salts include, but are not limited to, aluminum, calcium, lithium, magnesium, potassium, sodium, zinc, and diethanolamine salts.

According to some embodiments, the pharmaceutically acceptable salt may be a crystalline salt of (4S, 4aS, 5aR, 12aS)-4-dimethylamino-3, 10, 12, 12A-tetrahydroxy-7-[methoxy (methyl) amino)-methyl] acid amide. Such crystalline salt may be selected from the group consisting of mono hydrochloride, mono mesylate, and mono sulfate. These crystalline salts are described in U.S. Pat. No. 9,255,068, the contents of which are incorporated herein by reference in their entirety.

The term "raw material" as used herein, refers to a substance that is required to manufacture a product (e.g., sarecycline).

The term "reactor" or "batch reactor" or "chemical reactor" as used herein, refers to a vessel comprising a tank with an agitator and integral heating/cooling system used, for example, for the production of an active pharmaceutical ingredient. Reactors may vary in size, for example, from less than 1 liter to about 130,000 liters.

The term "reagent" as used herein, refers to a substance used in preparing a product because of its chemical activity.

The terms "soluble" and "solubility" as used herein, refer to the property of being susceptible to being dissolved in a specified fluid (solvent). The term "insoluble" refers to the property of a material that has minimal or limited solubility in a specified solvent. In a solution, the molecules of the solute (or dissolved substance) are uniformly distributed among those of the solvent. A "suspension" is a dispersion (mixture) in which a finely-divided species is combined with another species, with the former being so finely divided and mixed that it doesn't rapidly settle out. The most common suspensions are those of solids in liquid.

The term "solubilizing agents" as used herein, refers to those substances that enable solutes to dissolve.

The term "solution" as used herein, generally refers to a homogeneous mixture of two or more substances. It is frequently, though not necessarily, a liquid. In a solution, the molecules of the solute (or dissolved substance) are uniformly distributed among those of the solvent.

The term "solvate" as used herein, refers to a complex formed by the attachment of solvent molecules to that of a solute.

The term "solvent" as used herein, refers to a substance capable of dissolving another substance (termed a "solute") to form a uniformly dispersed mixture (solution).

The term "starting material" as used herein, refers to a raw material, intermediate, or a drug substance that is used in the production of a drug substance and that is incorporated as a significant structural fragment into the structure of the drug substance.

The term "stoichiometric" as used herein, refers to a quantitative relationship between two or more chemical substances undergoing a physical or chemical change.

The term "substance" as used herein, refers to a particular kind of material or matter having a specific composition and specific, uniform properties.

The term "tare" and its various grammatical forms as used herein, refers to a deduction from the gross weight of a substance and its container made in allowance for the weight of the container.

The term "wet cake" as used herein, refers to a substance, an ingredient, a component or a constituent that has been separated from a slurry (e.g., by filtration) and washed with water or an aqueous solution.

As used herein, a "wt. %" or "w/w %" or "weight percent" or "percent by weight" or "weight per weight percent" or percent weight per weight" of a component, unless specifically stated to the contrary, refers to the ratio of the weight of the component to the total weight of the composition, solution, mixture, etc. in which the component is included, expressed as a percentage.

The described invention provides a process for preparing sarecycline ((4S, 4aS, 5aR, 12aS)-4-dimethylamino-3, 10, 12, 12a-tetrahydroxy-7-[(methoxy (methyl) amino)-methyl]-1, 11-dioxo-1, 4, 4a, 5, 5a, 6, 11, 12a-octahydro-naphthacene-2-carboxylic acid amide) hydrochloride (HCl) (Formula I) and intermediates thereof.

According to some embodiments, the described invention provides a process for preparing sarecycline hydrochloride of Formula (I):

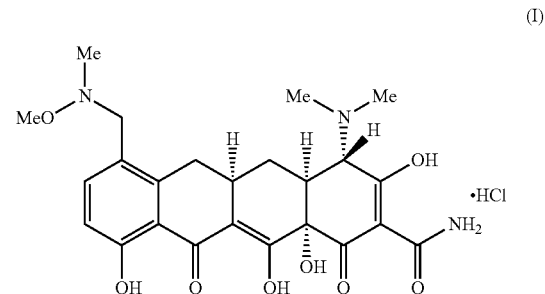 [SMILES: CON(C)Cc1ccc(O)c2c1C[C@H]1C[C@H]3[C@H](N(C)C)C(O)=C(C(N)=O)C(=O)[C@@]3(O)C(O)=C1C2=O ; Cl]

(I)

According to some embodiments, the process for preparing sarecycline hydrochloride (Formula I) comprises converting sancycline ((4S, 4aS, 5aR, 12aR)-4-(dimethyl-amino)-1, 10, 11, 12a-tetrahydroxy-3, 12-dioxo-4a, 5, 5a, 6-tetrahydro-4H-tetracene-2-carboxamide (Formula II) to sarecycline hydrochloride (Formula I).

According to some embodiments, the process for preparing sarecycline hydrochloride (Formula I) comprises four (4) steps.

According to some embodiments, the process for preparing sarecycline hydrochloride (Formula I) comprises an iodination step (Step 1).

According to some embodiments, Step 1 comprises reacting sancycline ((4S, 4aS, 5aR, 12aR)-4-(dimethylamino)-1, 10, 11, 12a-tetrahydroxy-3, 12-dioxo-4a, 5, 5a, 6-tetrahydro-4H-tetracene-2-carboxamide (Formula II) with trifluoroacetic acid (TFA) and N-iodosuccinimide (NIS) to form 7-iodosancycline trifluoroacetic acid salt (Formula III):

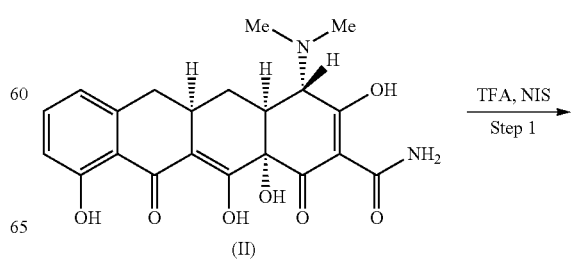

(II)

-continued

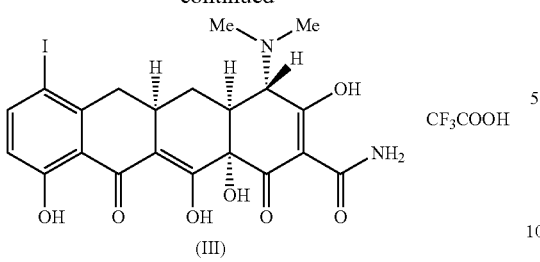

(III)

According to some embodiments, Step 1 comprises reacting sancycline ((4S, 4aS, 5aR, 12aR)-4-(dimethylamino)-1, 10, 11, 12a-tetrahydroxy-3, 12-dioxo-4a, 5, 5a, 6-tetrahydro-4H-tetracene-2-carboxamide (Formula II) with trifluoroacetic acid (TFA), N-iodosuccinimide (NIS) and Isopropanol (iPrOH) or tetrahydrofuran (THF) or Isopropanol (iPrOH) and tetrahydrofuran (THF) to form 7-iodosancycline trifluoroacetic acid salt (Formula III):

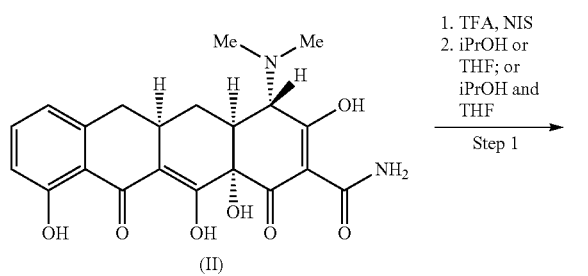

According to some embodiments, Step 1 comprises reacting sancycline ((4S, 4aS, 5aR, 12aR)-4-(dimethylamino)-1, 10, 11, 12a-tetrahydroxy-3, 12-dioxo-4a, 5, 5a, 6-tetrahydro-4H-tetracene-2-carboxamide (Formula II) with trifluoroacetic acid (TFA), N-iodosuccinimide (NIS), isopropanol and tetrahydrofuran (THF) to form 7-iodosancycline trifluoroacetic acid salt (Formula III):

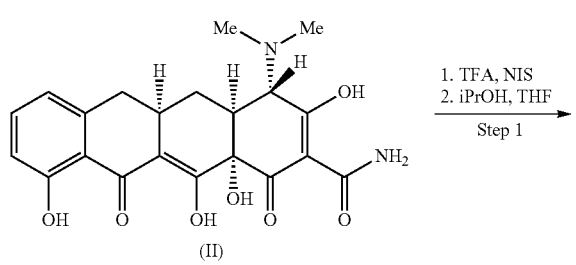

-continued

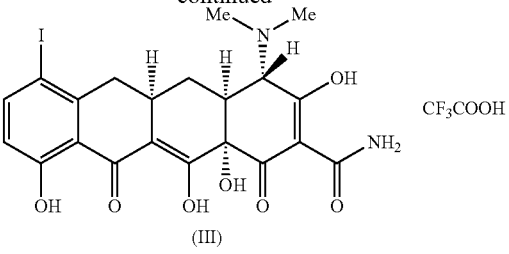

(III)

According to some embodiments, the amount of sancycline (Formula II) in Step 1 ranges from about 0.1 kg to about 10 kg. According to some embodiments, the amount of sancycline (Formula II) in Step 1 ranges from about 0.5 kg to about 5 kg. According to some embodiments, the amount of sancycline (Formula II) in Step 1 ranges from about 0.2 kg to about 2 kg. According to some embodiments, the amount of sancycline (Formula II) in Step 1 ranges from about 0.98 kg to about 1.02 kg. According to some embodiments, the amount of sancycline (Formula II) in Step 1 is about 1 kg.

According to some embodiments, the amount of trifluoroacetic acid (TFA) in Step 1 ranges from about 0.825 kg to about 82.5 kg. According to some embodiments, the amount of trifluoroacetic acid (TFA) in Step 1 ranges from about 4.125 kg to about 41.25 kg. According to some embodiments, the amount of trifluoroacetic acid (TFA) in Step 1 ranges from about 1.65 kg to about 16.5 kg. According to some embodiments, the amount of trifluoroacetic acid (TFA) in Step 1 ranges from about 8.09 kg to about 8.42 kg. According to some embodiments, the amount of trifluoroacetic acid (TFA) in Step 1 ranges from about 8.0 kg to about 8.5 kg. According to some embodiments, the amount of trifluoroacetic acid (TFA) in Step 1 is about 8.25 kg.

According to some embodiments, the amount of N-iodosuccinimide (NIS) in Step 1 ranges from about 0.0625 kg to about 6.25 kg. According to some embodiments, the amount of N-iodosuccinimide (NIS) in Step 1 ranges from about 0.3125 kg to about 3.125 kg. According to some embodiments, the amount of N-iodosuccinimide (NIS) in Step 1 ranges from about 0.125 kg to about 1.25 kg. According to some embodiments, the amount of N-iodosuccinimide (NIS) in Step 1 ranges from about 0.6125 kg to about 0.6375 kg. According to some embodiments, the amount of N-iodosuccinimide (NIS) in Step 1 ranges from about 0.60 kg to about 0.65 kg. According to some embodiments, the amount of N-iodosuccinimide (NIS) in Step 1 is about 0.625 kg.

According to some embodiments, the amount of isopropanol in Step 1 ranges from about greater than 0.09 kg to about greater than 9 kg. According to some embodiments, the amount of isopropanol in Step 1 ranges from about greater than 0.45 kg to about greater than 4.5 kg. According to some embodiments, the amount of isopropanol in Step 1 ranges from about greater than 0.18 kg to about greater than 1.8 kg. According to some embodiments, the amount of isopropanol in Step 1 ranges from about greater than 0.882 kg to about greater than 0.918 kg. According to some embodiments, the amount of isopropanol in Step 1 is greater than 0.9 kg. According to some embodiments, the amount of isopropanol in Step 1 is about 1 kg.

According to some embodiments, the amount of tetrahydrofuran (THF) in Step 1 ranges from about 0.9 kg to about 90 kg. According to some embodiments, the amount of tetrahydrofuran (THF) in Step 1 ranges from about 4.5 kg to about 45 kg. According to some embodiments, the amount of tetrahydrofuran (THF) in Step 1 ranges from about 1.80 kg to about 18 kg. According to some embodiments, the amount of tetrahydrofuran (THF) in Step 1 ranges from about 8.82 kg to about 9.18 kg. According to some embodiments, the amount of tetrahydrofuran (THF) in Step 1 is about 9 kg. According to some embodiments, the amount of tetrahydrofuran (THF) in Step 1 ranges from about greater than 1 to about greater than 100 kg. According to some embodiments, the amount of tetrahydrofuran (THF) in Step 1 ranges from about greater than 5.0 kg to about greater than 50 kg. According to some embodiments, the amount of tetrahydrofuran (THF) in Step 1 ranges from about greater than 2 kg to about greater than 20 kg. According to some embodiments, the amount of tetrahydrofuran (THF) in Step 1 ranges from about greater than 9.8 kg to about greater than 10.2 kg. According to some embodiments, the amount of tetrahydrofuran (THF) in Step 1 is about greater than 10 kg.

According to some embodiments, the theoretical yield of 7-iodosancyline trifluoroacetic acid salt (Formula III) is about 1.51 kg for every 1 kg of sancycline (Formula II). According to some embodiments, the observed yield of 7-iodosancyline trifluoroacetic acid salt (Formula III) ranges from about 40% to about 100% of the theoretical yield. According to some embodiments, the observed yield of 7-iodosancyline trifluoroacetic acid salt (Formula III) is about 65% of the theoretical yield. According to some embodiments, the observed yield of 7-iodosancyline trifluoroacetic acid salt (Formula III) ranges from about 0.604 kg to about 1.51 kg. According to some embodiments, the observed yield of 7-iodosancyline trifluoroacetic acid salt (Formula III) is about 0.982 kg.

According to some embodiments, the tetrahydrofuran (THF) in Step 1 increases the rate of crystallization of Formula III. According to some embodiments, the tetrahydrofuran (THF) in Step 1 purges the undesired impurities of the Formula III product. According to some embodiments, the tetrahydrofuran (THF) in Step 1 increases the yield and assay of Formula III. According to some embodiments, the tetrahydrofuran (THF) in Step 1 increases the purity of 7-iodosancycline (Formula III).

According to some embodiments, the process for preparing sarecycline hydrochloride (Formula I) comprises a palladium-catalyzed formylation step (Step 2).

According to some embodiments, Step 2 comprises reacting 7-iodosancycline trifluoroacetic acid salt (Formula III) with N-methyl pyrrolidone (NMP), triphenylphosphine (PPh₃), Bis-(Triphenyl Phosphine) palladium chloride catalyst (BTPP—PdCl₂), triethylsilane (Et₃SiH) and carbon monoxide (CO) to obtain 7-formylsancycline (Formula IV):

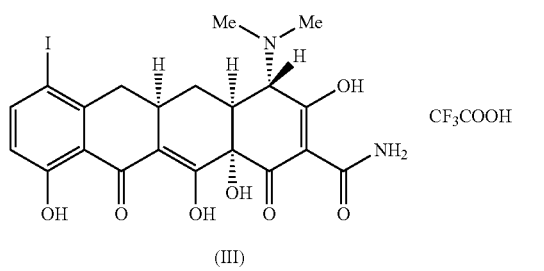

(III)

Step 2
1. NMP, PPh₃
2. BTPP—PdCl₂, ET₃SiH, CO

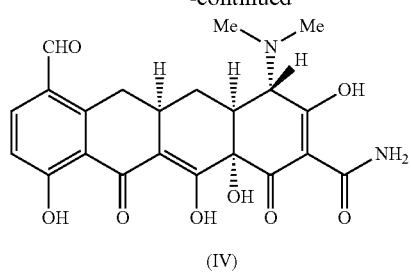

(IV)

According to some embodiments, Step 2 comprises reacting 7-iodosancycline trifluoroacetic acid salt (Formula III) with N-methyl pyrrolidone (NMP), triphenylphosphine (PPh₃), Bis-(Triphenyl Phosphine) palladium chloride catalyst (BTPP—PdCl₂), triethylsilane (Et₃SiH), carbon monoxide (CO) and sodium carbonate (Na₂CO₃), or cellulose or diatomaceous silica (SiO₂, e.g., Celite®) or water, or sulfuric acid (H₂SO₄) or ethanol (EtOH), or a combination thereof to obtain 7-formylsancycline (Formula IV):

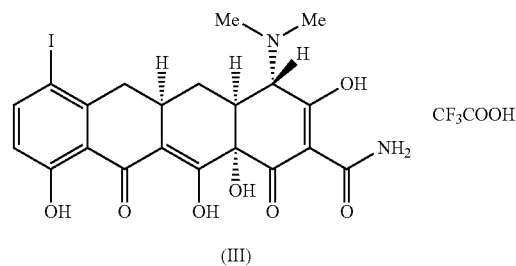

(III)

Step 2
1. NMP, PPh₃
2. BTPP—PdCl₂, ET₃SiH, CO
3. Na₂CO₃ or cellulose or SiO₂ or water or H₂SO₄ or EtOH or a combination thereof

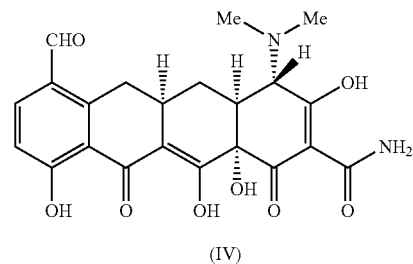

(IV)

According to some embodiments, Step 2 comprises reacting 7-iodosancycline trifluoroacetic acid salt (Formula III) with sodium carbonate (Na₂CO₃), cellulose or diatomaceous silica (SiO₂, e.g., Celite®), N-methyl pyrrolidone (NMP), triphenylphosphine (PPh₃), Bis-(Triphenyl Phosphine) palladium chloride catalyst (BTPP—PdCl₂), triethylsilane (Et₃SiH), carbon monoxide (CO), isolation through work-up using water, sulfuric acid (H₂SO₄) and ethanol (EtOH) to obtain 7-formylsancycline (Formula IV):

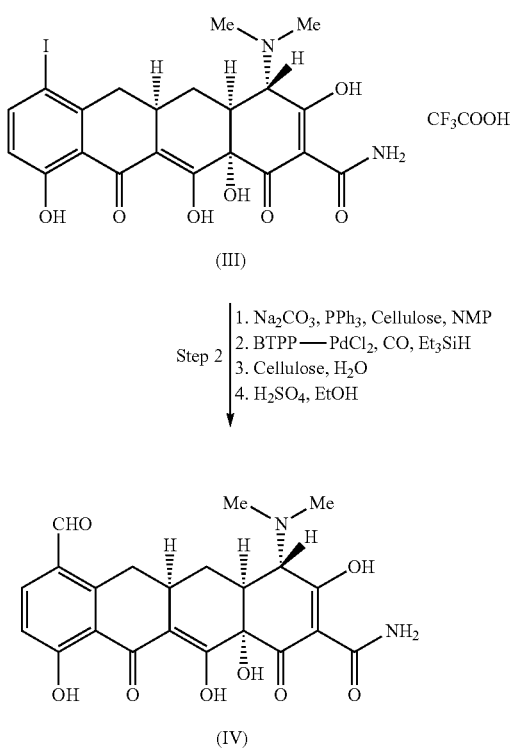

According to some embodiments, the amount of 7-iodosancycline trifluoroacetic acid salt (Formula III) in Step 2 ranges from about 0.1 kg to about 10 kg. According to some embodiments, the amount of 7-iodosancycline trifluoroacetic acid salt (Formula III) in Step 2 ranges from about 0.5 kg to about 5 kg. According to some embodiments, the amount of 7-iodosancycline trifluoroacetic acid salt (Formula III) in Step 2 ranges from about 0.2 kg to about 2 kg. According to some embodiments, the amount of 7-iodosancycline trifluoroacetic acid salt (Formula III) in Step 2 ranges from about 0.98 kg to about 1.02 kg. According to some embodiments, the amount of 7-iodosancycline trifluoroacetic acid salt (Formula III) in Step 2 is about 1 kg.

According to some embodiments, the amount of sodium carbonate ($Na_2CO_3$) in Step 2 ranges from about 0.034 kg to about 3.4 kg. According to some embodiments, the amount of sodium carbonate ($Na_2CO_3$) in Step 2 ranges from about 0.17 kg to about 1.7 kg. According to some embodiments, the amount of sodium carbonate ($Na_2CO_3$) in Step 2 ranges from about 0.068 kg to about 0.68 kg. According to some embodiments, the amount of sodium carbonate ($Na_2CO 3$) in Step 2 ranges from about 0.333 kg to about 0.347 kg. According to some embodiments, the amount of sodium carbonate ($Na_2CO_3$) in Step 2 ranges from about 0.32 kg to about 0.36 kg. According to some embodiments, the amount of sodium carbonate ($Na_2CO_3$) in Step 2 is about 0.34 kg.

According to some embodiments, the amount of cellulose or diatomaceous silica ($SiO_2$, e.g., Celite®) in Step 2 ranges from about 0.013 kg to about 1.3 kg. According to some embodiments, the amount of cellulose or diatomaceous silica ($SiO_2$, e.g., Celite®) in Step 2 ranges from about 0.065 kg to about 0.65 kg. According to some embodiments, the amount of cellulose or diatomaceous silica ($SiO_2$, e.g., Celite®) in Step 2 ranges from about 0.026 kg to about 0.26 kg. According to some embodiments, the amount of cellulose or diatomaceous silica ($SiO_2$, e.g., Celite®) in Step 2 ranges from about 0.1274 kg to about 0.1326 kg. According to some embodiments, the amount of cellulose or diatomaceous silica ($SiO_2$, e.g., Celite®) in Step 2 ranges from about 0.12 kg to about 0.15 kg. According to some embodiments, the amount of cellulose or diatomaceous silica ($SiO_2$, e.g., Celite®) in Step 2 is about 0.13 kg.

According to some embodiments, the amount of N-methyl pyrrolidone (NMP) in Step 2 ranges from about 0.225 kg to about 22.5 kg. According to some embodiments, the amount of N-methyl pyrrolidone (NMP) in Step 2 ranges from about 1.125 kg to about 11.25 kg. According to some embodiments, the amount of N-methyl pyrrolidone (NMP) in Step 2 ranges from about 0.45 kg to about 4.5 kg. According to some embodiments, the amount of N-methyl pyrrolidone (NMP) in Step 2 ranges from about 2.205 kg to about 2.295 kg. According to some embodiments, the amount of N-methyl pyrrolidone (NMP) in Step 2 ranges from about 2.10 kg to about 2.45 kg. According to some embodiments, the amount of N-methyl pyrrolidone (NMP) in Step 2 is about 2.25 kg.

According to some embodiments, the amount of triphenylphosphine ($PPh_3$) in Step 2 ranges from about 0.0008 kg to about 0.08 kg. According to some embodiments, the amount of triphenylphosphine ($PPh_3$) in Step 2 ranges from about 0.004 kg to about 0.04 kg. According to some embodiments, the amount of triphenylphosphine ($PPh_3$) in Step 2 ranges from about 0.0016 kg to about 0.016 kg. According to some embodiments, the amount of triphenylphosphine ($PPh_3$) in Step 2 ranges from about 0.0784 kg to about 0.00816 kg. According to some embodiments, the amount of triphenylphosphine ($PPh_3$) in Step 2 ranges from about 0.0075 kg to about 0.0085 kg. According to some embodiments, the amount of triphenylphosphine ($PPh_3$) in Step 2 is about 0.008 kg.

According to some embodiments, the amount of Bis-(Triphenyl Phosphine) palladium chloride catalyst (BTPP—$PdCl_2$) in Step 2 ranges from about 0.00028 kg to about 0.028 kg. According to some embodiments, the amount of Bis-(Triphenyl Phosphine) palladium chloride catalyst (BTPP—$PdCl_2$) in Step 2 ranges from about 0.0014 kg to about 0.014 kg. According to some embodiments, the amount of Bis-(Triphenyl Phosphine) palladium chloride catalyst (BTPP—$PdCl_2$) in Step 2 ranges from about. 00056 kg to about 0.0056 kg. According to some embodiments, the amount of Bis-(Triphenyl Phosphine) palladium chloride catalyst (BTPP—$PdCl_2$) in Step 2 ranges from about 0.00274 kg to about 0.00286 kg. According to some embodiments, the amount of Bis-(Triphenyl Phosphine) palladium chloride catalyst (BTPP—$PdCl_2$) in Step 2 ranges from about 0.0022 kg to about 0.0034 kg. According to some embodiments, the amount of Bis-(Triphenyl Phosphine) palladium chloride catalyst (BTPP—$PdCl_2$) in Step 2 is about 0.0028 kg. According to some embodiments, the amount of Bis-(Triphenyl Phosphine) palladium chloride catalyst (BTPP—$PdCl_2$) in Step 2 is about 0.26%+0.05% mol/mol of palladium chloride catalyst.

According to some embodiments, the amount of triethylsilane ($Et_3SiH$) in Step 2 ranges from about 0.022 kg to about 2.2 kg. According to some embodiments, the amount of triethylsilane (Et$_3$SiH) in Step 2 ranges from about 0.11 kg to about 1.1 kg. According to some embodiments, the amount of triethylsilane (Et$_3$SiH) in Step 2 ranges from about 0.044 kg to about 0.44 kg. According to some embodiments, the amount of triethylsilane (Et$_3$SiH) in Step 2 ranges from about 0.2156 kg to about 0.2244 kg. According to some embodiments, the amount of triethylsilane (Et$_3$SiH) in Step 2 ranges from about 0.20 kg to about 0.24 kg. According to some embodiments, the amount of triethylsilane (Et$_3$SiH) in Step 2 is about 0.22 kg.

According to some embodiments, the amount of water in Step 2 ranges from about 0.58 kg to about 58 kg. According to some embodiments, the amount of water in Step 2 ranges from about 2.9 kg to about 29 kg. According to some embodiments, the amount of water in Step 2 ranges from about 1.16 kg to about 11.6 kg. According to some embodiments, the amount of water in Step 2 ranges from about 5.684 kg to about 5.916 kg. According to some embodiments, the amount of water in Step 2 ranges from about 5.7 kg to about 5.85. According to some embodiments, the amount of water in Step 2 ranges from about 0.90 kg to about 1.1 kg. According to some embodiments, the amount of water in Step 2 is about 5.8 kg. According to some embodiments, the amount of water in Step 2 is about 1 kg.

According to some embodiments, the amount of ethanol (EtOH) in Step 2 ranges from about 0.2 kg to about 20 kg. According to some embodiments, the amount of ethanol (EtOH) in Step 2 ranges from about 1 kg to about 10 kg. According to some embodiments, the amount of ethanol (EtOH) in Step 2 ranges from about 0.4 kg to about 4 kg. According to some embodiments, the amount of ethanol (EtOH) in Step 2 ranges from about 1.96 kg to 2.04 kg. According to some embodiments, the amount of ethanol (EtOH) in Step 2 ranges from about 0.55 kg to about 2 kg. According to some embodiments, the amount of ethanol (EtOH) in Step 2 is about 2 kg.

According to some embodiments, the theoretical yield of 7-formylsancycline (Formula IV) is about 0.67 kg for every 1 kg of 7-iodosancycline trifluoroacetic acid salt (Formula III). According to some embodiments, the observed yield of 7-formylsancycline (Formula IV) ranges from about 60% to about 80% of the theoretical yield. According to some embodiments, the observed yield of 7-formylsancycline (Formula IV) is about 75% of the theoretical yield. According to some embodiments, the observed yield of 7-formylsancycline (Formula IV) ranges from about 0.402 kg to about 0.536 kg. According to some embodiments, the observed yield of 7-formylsancycline (Formula IV) is about 0.5025 kg.

According to some embodiments, the N-methyl pyrrolidone (NMP) in Step 2 reduces gel formation. According to some embodiments, the N-methyl pyrrolidone (NMP) in Step 2 provides a suitable solvent medium for the conversion of Formula III to Formula IV to completion.

According to some embodiments, in Step 2 of the process for preparing the sarecycline hydrochloride via Scheme 1 (see Example 1), the suspension of sodium carbonate (NaCO$_3$), cellulose or SiO$_2$ and N-methyl pyrrolidone (NMF) is stirred at ambient temperature under nitrogen atmosphere until the oxygen content is less than or equal to 200 parts per billion (ppb). In some embodiments, the oxygen content reaches 200 ppb.

According to some embodiments, in Step 2 of the process for preparing the sarecycline hydrochloride via Scheme 1 (see Example 1), the suspension of sodium carbonate (NaCO$_3$), cellulose or SiO$_2$ and N-methyl pyrrolidone (NMF) is stirred at ambient temperature under nitrogen atmosphere until the oxygen content is less than or equal to 1000 parts per billion (ppb). In some embodiments, the oxygen content reaches 1000 ppb.

According to some embodiments, in Step 2 of the process for preparing the sarecycline hydrochloride via Scheme 2 (see Example 2), sodium carbonate, cellulose or SiO$_2$ and N-methyl pyrrolidone (NMP) are charged to a suitable nitrogen purged reactor (R1) and the resulting suspension is stirred at 25° C.±5° C. In some embodiments, R1 is purged with nitrogen until the oxygen content is less than or equal to 200 ppb. Then, in some embodiments, R1 is charged with triphenylphosphine (PPh$_3$), followed by Iodosancycline, while maintaining the temperature at 25° C.±5° C. Next, in some embodiments, Bis-(Triphenyl Phosphine) palladium chloride catalyst (BTPP—PdCl2; 0.26%±0.05%, mol/mol) is added to R1 while maintaining an oxygen content of less than or equal to 200 ppb. In some embodiments, the contents of R1 are then transferred to another clean reactor (R2) at 25° C.±5° C. under vacuum. In some embodiments, the oxygen content of R2 is less than or equal to 200 ppb.

According to some embodiments, in Step 2 of the process for preparing the sarecycline hydrochloride via Scheme 2 (see Example 2), sodium carbonate, cellulose or SiO$_2$ and N-methyl pyrrolidone (NMP) are charged to a suitable nitrogen purged reactor (R1) and the resulting suspension is stirred at 25° C.±5° C. In some embodiments, R1 is purged with nitrogen until the oxygen content is less than or equal to 1000 ppb. Then, in some embodiments, R1 is charged with triphenylphosphine (PPh$_3$), followed by Iodosancycline, while maintaining the temperature at 25° C.±5° C. Next, in some embodiments, Bis-(Triphenyl Phosphine) palladium chloride catalyst (BTPP—PdCl2; 0.26%+0.05%, mol/mol) is added to R1 while maintaining an oxygen content of less than or equal to 1000 ppb. In some embodiments, the contents of R1 are then transferred to another clean reactor (R2) at 25° C.±5° C. under vacuum. In some embodiments, the oxygen content of R2 is less than or equal to 1000 ppb.

According to some embodiments, the process for preparing sarecycline hydrochloride (Formula I) comprises a reductive amination step (Step 3a).

According to some embodiments, Step 3a comprises reacting 7-formylsancycline (Formula IV) with dimethylhydroxylamine (DMHA or NH(Me) OMe) free base, in the presence of oxalic acid, using dimethylaminoborane (DMAB or BH$_3$-dimethylamine) as a reducing agent and quenching the reaction with acetone to produce sarecycline crude oxalate salt (Formula V):

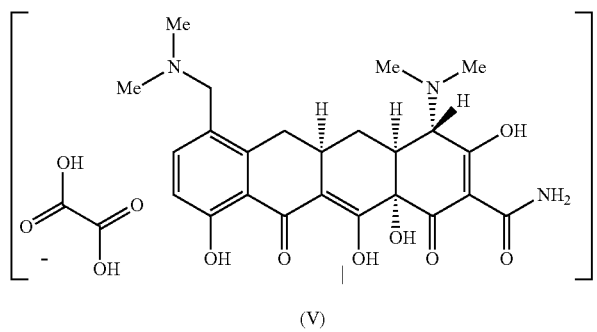

(V)

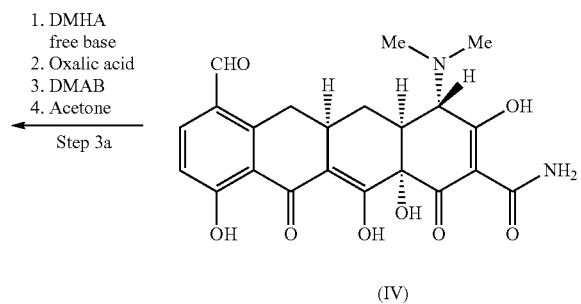

(IV)

According to some embodiments, Step 3a comprises reacting 7-formylsancycline (Formula IV) with dimethylhydroxylamine (DMHA or NH(Me) OMe) free base, methanol (MeOH), in the presence of oxalic acid, using dimethylaminoborane (DMAB or $BH_3$-dimethylamine) as a reducing agent and quenching the reaction with acetone to produce sarecycline crude oxalate salt (Formula V):

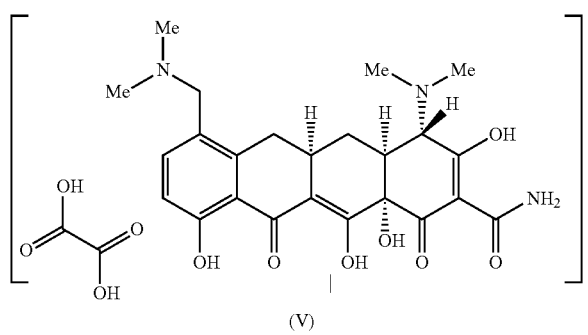

(V)

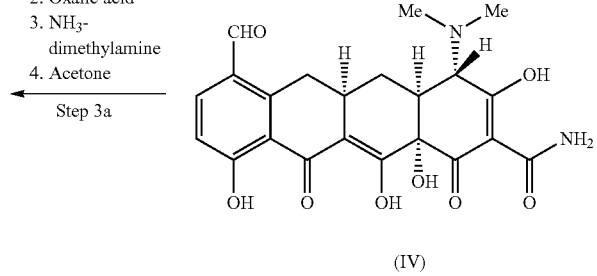

(IV)

According to some embodiments, the amount of 7-formylsancycline (Formula IV) in Step 3a ranges from about 0.1 kg to about 10 kg. According to some embodiments, the amount of 7-formylsancycline (Formula IV) in Step 3a ranges from about 0.5 kg to about 5 kg. According to some embodiments, the amount of 7-formylsancycline (Formula IV) in Step 3a ranges from about 0.2 kg to about 2 kg. According to some embodiments, the amount of 7-formylsancycline (Formula IV) in Step 3a ranges from about 0.98 kg to about 1.02 kg. According to some embodiments, the amount of 7-formylsancycline (Formula IV) in Step 3a is about 1 kg.

According to some embodiments, the amount of dimethylhydroxylamine (DMHA or NH(Me) OMe) free base in Step 3a ranges from about 0.05 kg to about 5 kg. According to some embodiments, the amount of dimethylhydroxylamine (DMHA or NH(Me) OMe) free base in Step 3a ranges from about 0.25 kg to about 2.5 kg. According to some embodiments, the amount of dimethylhydroxylamine (DMHA or NH(Me) OMe) free base in Step 3a ranges from about 0.1 kg to about 1 kg. According to some embodiments, the amount of dimethylhydroxylamine (DMHA or NH(Me) OMe) free base in Step 3a ranges from about 0.49 kg to about 0.51 kg. According to some embodiments, the amount of dimethylhydroxylamine (DMHA or NH(Me) OMe) free base in Step 3a ranges from about 0.49 kg to about 0.52 kg. According to some embodiments, the amount of dimethylhydroxylamine (DMHA or NH(Me) OMe) free base in Step 3a is about 0.5 kg.

According to some embodiments, the amount of methanol (MeOH) in Step 3a ranges from about 0.28 kg to about 28 kg. According to some embodiments, the amount of methanol (MeOH) in Step 3a ranges from about 1.4 kg to about 14 kg. According to some embodiments, the amount of methanol (MeOH) in Step 3a ranges from about 0.56 kg to about 5.6 kg. According to some embodiments, the amount of methanol (MeOH) in Step 3a ranges from about 2.744 kg to about 2.856 kg. According to some embodiments, the amount of methanol (MeOH) in Step 3a ranges from about 2.75 kg to about 2.85 kg. According to some embodiments, the amount of methanol (MeOH) in Step 3a is about 2.8 kg.

According to some embodiments, the amount of oxalic acid in Step 3a ranges from about 0.098 kg to about 9.8 kg. According to some embodiments, the amount of oxalic acid in Step 3a ranges from about 0.49 kg to about 4.9 kg. According to some embodiments, the amount of oxalic acid in Step 3a ranges from about 0.196 kg to about 1.96 kg. According to some embodiments, the amount of oxalic acid in Step 3a ranges from about 0.941 kg to about 1 kg. According to some embodiments, the amount of oxalic acid in Step 3a ranges from about 0.95 kg to about 1 kg. According to some embodiments, the amount of oxalic acid in Step 3a is about 1 kg.

According to some embodiments, the amount of dimethylaminoborane (DMAB or $BH_3$-dimethylamine) in Step 3a ranges from about 0.018 kg to about 1.8 kg. According to some embodiments, the amount of dimethylaminoborane (DMAB or $BH_3$-dimethylamine) in Step 3a ranges from about 0.09 kg to about 0.9 kg. According to some embodiments, the amount of dimethylaminoborane (DMAB or $BH_3$-dimethylamine) in Step 3a ranges from about 0.036 kg to about 0.36 kg. According to some embodiments, the amount of dimethylaminoborane (DMAB or $BH_3$-dimethylamine) in Step 3a ranges from about 0.1764 kg to about 0.1836 kg. According to some embodiments, the amount of dimethylaminoborane (DMAB or BH₃-dimethylamine) in Step 3a ranges from about 0.175 kg to about 0.185 kg. According to some embodiments, the amount of dimethylaminoborane (DMAB or BH₃-dimethylamine) in Step 3a is about 0.18 kg.

According to some embodiments, the amount of acetone in Step 3a ranges from about greater than 0.22 kg to about greater than 22 kg. According to some embodiments, the amount of acetone in Step 3a ranges from about greater than 1.1 kg to about greater than 11 kg. According to some embodiments, the amount of acetone in Step 3a ranges from about greater than 0.44 kg to about greater than 4.4 kg. According to some embodiments, the amount of acetone in Step 3a ranges from about greater than 2.156 kg to about greater than 2.244 kg. According to some embodiments, the amount of acetone in Step 3a ranges from about greater than 2.2 kg to about greater than 2.4 kg. According to some embodiments, the amount of acetone in Step 3a is about greater than 2.2 kg. According to some embodiments, the amount of acetone in Step 3a is about greater than 2.4 kg.

According to some embodiments, the sarecycline crude oxalate salt (Formula V) is isolated. According to some embodiments, the sarecycline crude oxalate salt (Formula V) is not isolated. According to some embodiments, the sarecycline crude oxalate salt is a non-isolated intermediate processed through a neutralization procedure (Step 3b).

According to some embodiments, the process for preparing sarecycline hydrochloride (Formula I) comprises a neutralization of sarecycline crude oxalate salt to sarecycline free base (Step 3b).

According to some embodiments, Step 3b comprises reacting sarecycline crude oxalate salt (Formula V) with ammonium hydroxide (NH₃ (aq.)) or hydrochloric acid (HCl) to produce sarecycline free base (Formula VI):

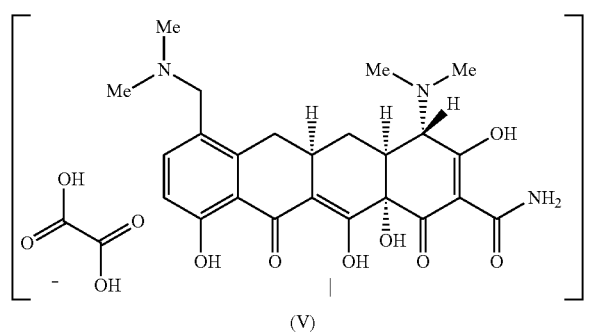

According to some embodiments, Step 3b comprises reacting sarecycline crude oxalate salt (Formula V) with ammonium hydroxide (NH₃ (aq.)) or hydrochloric acid (HCl) and cellulose or diatomaceous silica (SiO₂, e.g., Celite®) or dichloromethane (DCM) or water or methanol (MeOH) or acetone or a combination thereof to produce sarecycline free base (Formula VI):

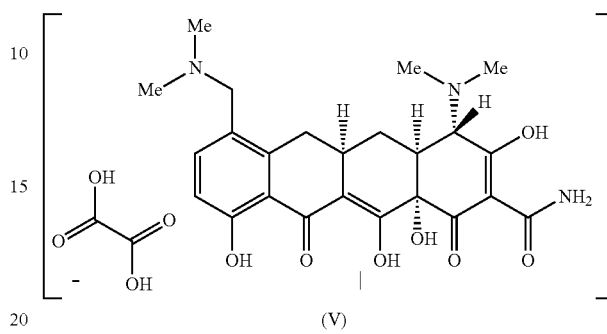

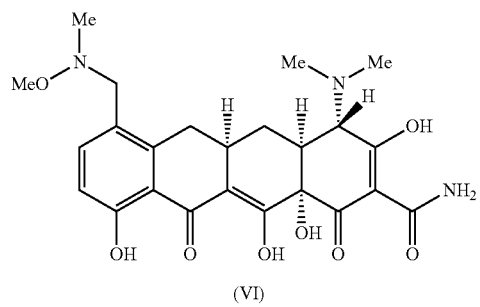

According to some embodiments, Step 3b comprises reacting sarecycline crude oxalate salt (Formula V) with ammonium hydroxide (NH₃ (aq.)), hydrochloric acid (HCl) and cellulose or diatomaceous silica (SiO₂, e.g., Celite®) or dichloromethane (DCM) or water or methanol (MeOH) or acetone or a combination thereof to produce sarecycline free base (Formula VI):

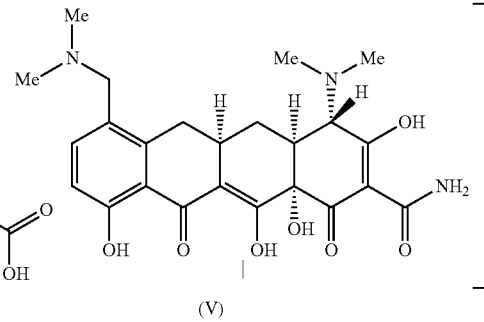

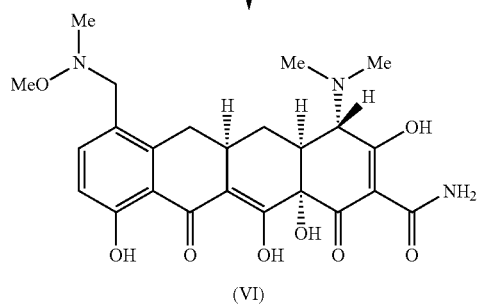

-continued

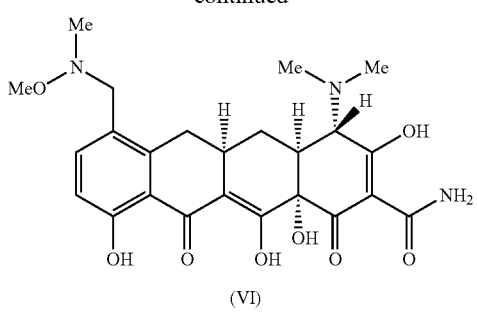

(VI)

According to some embodiments, Step 3b comprises reacting sarecycline crude oxalate salt (Formula V) with cellulose or diatomaceous silica (SiO₂, e.g., Celite®), dichloromethane (DCM), ammonium hydroxide (NH₃ (aq.)) or hydrochloric acid (HCl), water, methanol (MeOH) and acetone to produce sarecycline free base (Formula VI):

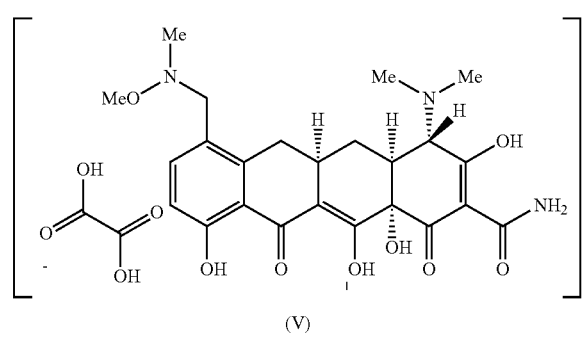

According to some embodiments, Step 3b comprises reacting sarecycline crude oxalate salt (Formula V) with cellulose or diatomaceous silica (SiO₂, e.g., Celite®), dichloromethane (DCM), ammonium hydroxide (NH₃ (aq.)), hydrochloric acid (HCl), water, methanol (MeOH) and acetone to produce sarecycline free base (Formula VI):

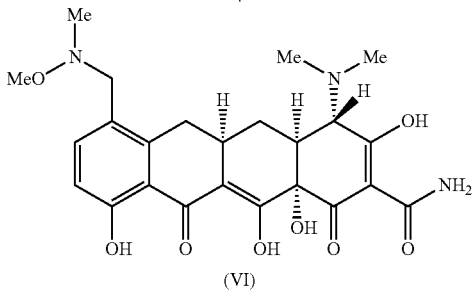

According to some embodiments, the amount of sarecycline crude oxalate salt (Formula V) in Step 3b ranges from about 0.1 kg to about 10 kg. According to some embodiments, the amount of sarecycline crude oxalate salt (Formula V) in Step 3b ranges from about 0.5 kg to about 5 kg. According to some embodiments, the amount of sarecycline crude oxalate salt (Formula V) in Step 3b ranges from about 0.2 kg to about 2 kg. According to some embodiments, the amount of sarecycline crude oxalate salt (Formula V) in Step 3b ranges from about 0.98 kg to about 1.02 kg. According to some embodiments, the amount of sarecycline crude oxalate salt (Formula V) in Step 3b is about 1 kg.

According to some embodiments, the amount of cellulose or diatomaceous silica (SiO₂, e.g., Celite®) in Step 3b ranges from about 0.027 kg to about 2.7 kg. According to some embodiments, the amount of cellulose or diatomaceous silica (SiO₂, e.g., Celite®) in Step 3b ranges from about 0.135 kg to about 1.35 kg. According to some embodiments, the amount of cellulose or diatomaceous silica (SiO₂, e.g., Celite®) in Step 3b ranges from about 0.054 kg to about 0.54 kg. According to some embodiments, the amount of cellulose or diatomaceous silica (SiO₂, e.g., Celite®) in Step 3b ranges from about 0.2646 kg to about 0.2754 kg. According to some embodiments, the amount of cellulose or diatomaceous silica (SiO₂, e.g., Celite®) in Step 3b ranges from about 0.26 kg to about 0.29 kg. According to some embodiments, the amount of cellulose or diatomaceous silica (SiO₂, e.g., Celite®) in Step 3b is about 0.27 kg.

According to some embodiments, the amount of dichloromethane (DCM) in Step 3b ranges from about greater than 0.9 kg to about greater than 90 kg. According to some embodiments, the amount of dichloromethane (DCM) in Step 3b ranges from about greater than 4.5 kg to about greater than 45 kg. According to some embodiments, the amount of dichloromethane (DCM) in Step 3b ranges from about greater than 1.8 kg to about greater than 18 kg.

According to some embodiments, the amount of dichloromethane (DCM) in Step 3b ranges from about greater than 8.82 kg to about greater than 9.18 kg. According to some embodiments, the amount of dichloromethane (DCM) in Step 3b ranges from about 1.8 kg to about 2.7 kg. According to some embodiments, the amount of dichloromethane (DCM) in Step 3b is about greater than 9 kg. According to some embodiments, the amount of dichloromethane (DCM) in Step 3b ranges from about greater than 0.1 kg to about greater than 10 kg. According to some embodiments, the amount of dichloromethane (DCM) in Step 3b ranges from about greater than 0.5 kg to about greater than 5 kg. According to some embodiments, the amount of dichloromethane (DCM) in Step 3b ranges from about greater than 0.2 kg to about greater than 2 kg. According to some embodiments, the amount of dichloromethane (DCM) in Step 3b ranges from about greater than 0.98 kg to about greater than 1.02 kg. According to some embodiments, the amount of dichloromethane (DCM) in Step 3b is about greater than 1 kg. According to some embodiments, the amount of dichloromethane (DCM) in Step 3b is about 2.3 kg.

According to some embodiments, the amount of water in Step 3b ranges from about greater than 0.8 kg to about greater than 80 kg. According to some embodiments, the amount of water in Step 3b ranges from about greater than 4 kg to about greater than 40 kg. According to some embodiments, the amount of water in Step 3b ranges from about greater than 1.6 kg to about greater than 16 kg. According to some embodiments, the amount of water in Step 3b ranges from about greater than 7.84 kg to about greater than about 8.16 kg. According to some embodiments, the amount of water in Step 3b is about greater than 8 kg. According to some embodiments, the amount of water in Step 3b ranges from about greater than 0.5 kg to about greater than 80 kg. According to some embodiments, the amount of water in Step 3b ranges from about greater than 2.5 kg to about greater than 25 kg. According to some embodiments, the amount of water in Step 3b ranges from about greater than 1 kg to about greater than 10 kg. According to some embodiments, the amount of water in Step 3b ranges from about greater than 4.9 kg to about greater than about 5.1 kg. According to some embodiments, the amount of water in Step 3b is about greater than 5 kg.

According to some embodiments, the amount of methanol (MeOH) in Step 3b ranges from about 0.055 kg to about 5.5 kg. According to some embodiments, the amount of methanol (MeOH) in Step 3b ranges from about 0.275 kg to about 2.75 kg. According to some embodiments, the amount of methanol (MeOH) in Step 3b ranges from about 0.11 kg to about 1.1 kg. According to some embodiments, the amount of methanol (MeOH) in Step 3b ranges from about 0.539 kg to about 0.561 kg. According to some embodiments, the amount of methanol (MeOH) in Step 3b ranges from about 0.37 kg to about 0.75 kg. According to some embodiments, the amount of methanol (MeOH) in Step 3b is about 0.55 kg.

According to some embodiments, the amount of acetone in Step 3b ranges from about greater than 0.3 kg to about greater than 30 kg. According to some embodiments, the amount of acetone in Step 3b ranges from about greater than 1.5 kg to about greater than 15 kg. According to some embodiments, the amount of acetone in Step 3b ranges from about greater than 0.6 kg to about greater than 6 kg. According to some embodiments, the amount of acetone in Step 3b ranges from about greater than 2.94 kg to about greater than 3.06 kg. According to some embodiments, the amount of acetone in Step 3b is about greater than 3 kg. According to some embodiments, the amount of acetone in Step 3b ranges from about greater than 0.32 kg to about greater than 32 kg. According to some embodiments, the amount of acetone in Step 3b ranges from about greater than 1.6 kg to about greater than 16 kg. According to some embodiments, the amount of acetone in Step 3b ranges from about greater than 0.64 kg to about greater than 6.4 kg. According to some embodiments, the amount of acetone in Step 3b ranges from about greater than 3.136 kg to about greater than 3.264 kg. According to some embodiments, the amount of acetone in Step 3b is about greater than 3.2 kg. According to some embodiments, the amount of acetone in Step 3b ranges from about 0.075 kg to about 7.5 kg. According to some embodiments, the amount of acetone in Step 3b ranges from about 0.375 kg to about 3.75 kg. According to some embodiments, the amount of acetone in Step 3b ranges from about 0.15 kg to about 1.5 kg. According to some embodiments, the amount of acetone in Step 3b ranges from about 0.735 kg to about 0.765 kg. According to some embodiments, the amount of acetone in Step 3b is about 0.75 kg.

According to some embodiments, the theoretical yield of sarecycline free base (Formula VI) is about 1.1 kg for every 1 kg of 7-formylsancycline (Formula IV). According to some embodiments, the observed yield of sarecycline free base (Formula VI) ranges from about 35% to about 68% of the theoretical yield. According to some embodiments, the observed yield of sarecycline free base (Formula VI) is about 60% of the theoretical yield. According to some embodiments, the observed yield of sarecycline free base (Formula VI) ranges from about 0.385 kg to about 0.748 kg. According to some embodiments, the observed yield of sarecycline free base (Formula VI) is about 0.66 kg.

According to some embodiments, the sarecycline free base (Formula VI) can be reprocessed. According to some embodiments, the sarecycline free base (Formula VI) can be reprocessed by repeating Step 3b. According to some embodiments, the sarecycline free base (Formula VI) can be reprocessed by repeating Step 3b at least one time. According to some embodiments, the sarecycline free base (Formula VI) can be reprocessed by repeating Step 3b until in-process specifications are met for sancyline impurity levels, 7-formylsancycline impurity levels, 4R-epimer impurity levels or a combination thereof. 4R-epimer impurities may include, but are not limited to, 4R-epimer-9-iodosancycline, 4R-epimer-7-iodosancycline, 4R-epimer-7,9-bisiodosancycline, 4R-epimer-7-formylsancycline and 4R-sarecycline. According to some embodiments, the sarecycline free base (Formula VI) can be reprocessed by repeating Step 3b when sancyline impurity levels are about >1% (w/w %). According to some embodiments, the sarecycline free base (Formula VI) can be reprocessed by repeating Step 3b when 7-formylsancycline impurity levels are about >1% (w/w %). According to some embodiments, the sarecycline free base (Formula VI) can be reprocessed by repeating Step 3b when 4R-epimer-7-formylsancycline impurity levels are about >1.0% (w/w %). According to some embodiments, the sarecycline free base (Formula VI) can be reprocessed by repeating Step 3b when 4R-sarecycline impurity levels are about >1.5% (w/w %).

According to some embodiments, the sarecycline free base (Formula VI) can be reworked. According to some embodiments, the sarecycline free base (Formula VI) can be reworked by treating sarecycline free base with trifluoroacetic acid (TFA), water, isopropanol and tetrahydrofuran (THF) and then repeating step 3b. According to some embodiments, the sarecycline free base (Formula VI) can be reworked at least one time. According to some embodiments, the sarecycline free base (Formula VI) can be reworked until in-process specifications are met for sancycline impurity levels, 7-formylsancycline impurity levels, 4R-epimer impurity levels, 7-methoxyiminomethyl impurity or a combination thereof. According to some embodiments, the sarecycline free base (Formula VI) can be reworked when sancycline impurity levels are about >1% (w/w %). According to some embodiments, the sarecycline free base (Formula VI) can be reworked when 7-formylsancycline impurity levels are about >1% (w/w %). According to some embodiments, the sarecycline free base (Formula VI) can be reworked when 4R-epimer-7-formylsancycline impurity levels are about >1.0% (w/w %). According to some embodiments, the sarecycline free base (Formula VI) can be reworked when 4R-sarecycline impurity levels are about >1.5% (% w/w).

According to some embodiments, the process for preparing sarecycline hydrochloride (Formula I) comprises conversion of sarecycline free base to sarecycline hydrochloride salt (Step 4).

According to some embodiments, Step 4 comprises reacting sarecycline free base (Formula VI) with ethanolic hydrochloric acid solution to form sarecycline hydrochloride (Formula I):

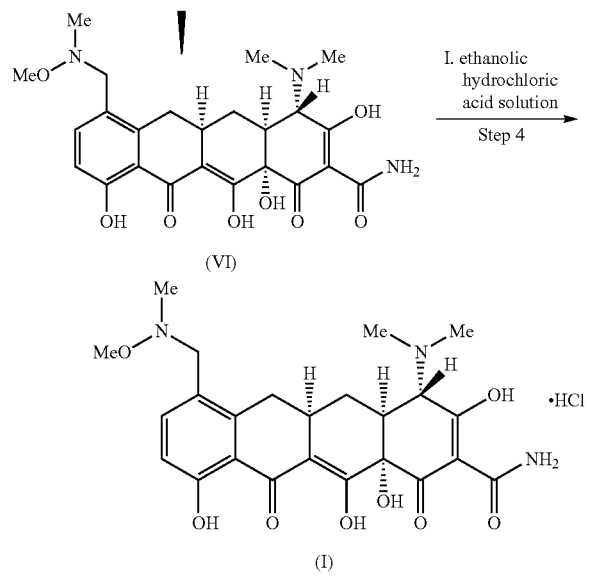

According to some embodiments, Step 4 comprises reacting sarecycline free base (Formula VI) with an ethanolic hydrochloric acid solution and ethanol (EtOH) or water or hydrochloric acid (HCl) or a combination thereof to form sarecycline hydrochloride (Formula I):

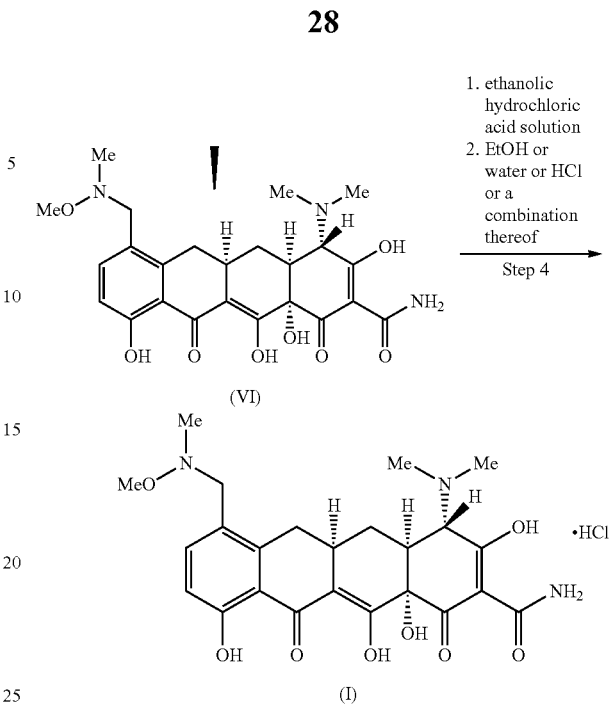

According to some embodiments, Step 4 comprises reacting sarecycline free base (Formula VI) with ethanol (EtOH), water, hydrochloric acid (HCl) and ethanolic hydrochloric acid solution to form sarecycline hydrochloride (Formula I):

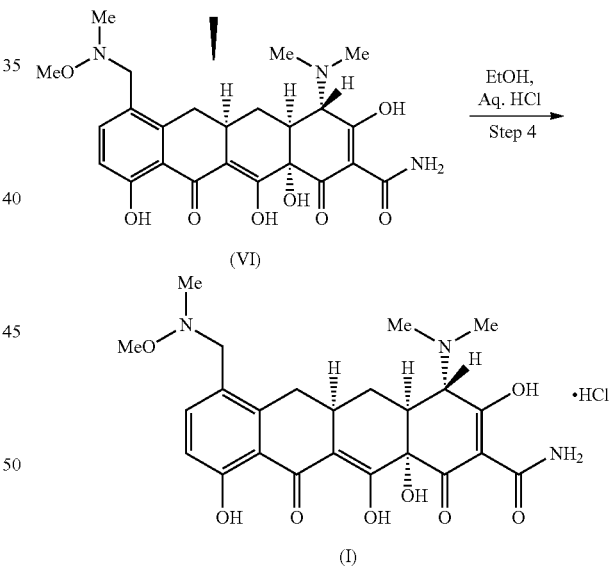

According to some embodiments, the amount of sarecycline free base (Formula VI) in Step 4 ranges from about 0.1 kg to about 10 kg. According to some embodiments, the amount of sarecycline free base (Formula VI) in Step 4 ranges from about 0.5 kg to about 5 kg. According to some embodiments, the amount of sarecycline free base (Formula VI) in Step 4 ranges from about 0.2 kg to about 2 kg. According to some embodiments, the amount of sarecycline free base (Formula VI) in Step 4 ranges from about 0.98 kg to about 1.02 kg. According to some embodiments, the amount of sarecycline free base (Formula VI) in Step 4 in Step 3b is about 1 kg.

According to some embodiments, the amount of ethanol (EtOH) in Step 4 ranges from about 2.86 kg to about 143 kg. According to some embodiments, the amount of ethanol (EtOH) in Step 4 ranges from about 7.15 kg to about 71.5 kg. According to some embodiments, the amount of ethanol (EtOH) in Step 4 ranges from about 2.86 kg to about 28.6 kg. According to some embodiments, the amount of ethanol (EtOH) in Step 4 ranges from about 14.01 kg to about 14.59 kg. According to some embodiments, the amount of ethanol (EtOH) in Step 4 ranges from about 14 kg to about 14.6 kg. According to some embodiments, the amount of ethanol (EtOH) in Step 4 is about 14.3 kg.

According to some embodiments, the amount of ethanol (EtOH) used to prepare ethanolic HCl solution in Step 4 ranges from about 0.032 kg to about 3.2 kg. According to some embodiments, the amount of ethanol (EtOH) used to prepare ethanolic HCl solution in Step 4 ranges from about 0.16 kg to about 1.6 kg. According to some embodiments, the amount of ethanol (EtOH) used to prepare ethanolic HCl solution in Step 4 ranges from about 0.064 kg to about 0.64 kg. According to some embodiments, the amount of ethanol (EtOH) used to prepare ethanolic HCl solution in Step 4 ranges from about 0.314 kg to about 0.326 kg. According to some embodiments, the amount of ethanol (EtOH) used to prepare ethanolic HCl solution in Step 4 ranges from about 0.29 kg to about 0.35 kg. According to some embodiments, the amount of ethanol (EtOH) used to prepare ethanolic HCl solution in Step 4 is about 0.32 kg.

According to some embodiments, Step 4 comprises a cake rinse. According to some embodiments, the cake rinse is performed with ethanol (EtOH). According to some embodiments, the amount of ethanol (EtOH) used for the cake rinse in Step 4 ranges from about greater than or equal to 0.3 kg to about greater than or equal to 30 kg. According to some embodiments, the amount of ethanol (EtOH) used for the cake rinse in Step 4 ranges from about greater than or equal to 1.5 kg to about greater than or equal to 15 kg. According to some embodiments, the amount of ethanol (EtOH) used for the cake rinse in Step 4 ranges from about greater than or equal to 0.6 kg to about greater than or equal to 6 kg. According to some embodiments, the amount of ethanol (EtOH) used for the cake rinse in Step 4 ranges from about greater than or equal to 2.94 kg to about greater than or equal to 3.06 kg. According to some embodiments, the amount of ethanol (EtOH) used for the cake rinse in Step 4 is about greater than or equal to 3 kg.

According to some embodiments, the amount of water in Step 4 ranges from about 0.018 kg to about 1.8 kg. According to some embodiments, the amount of water in Step 4 ranges from about 0.09 kg to about 0.9 kg. According to some embodiments, the amount of water in Step 4 ranges from about 0.036 kg to about 0.36 kg. According to some embodiments, the amount of water in Step 4 ranges from about 0.1764 kg to about 0.1836 kg. According to some embodiments, the amount of water in Step 4 ranges from about 0.15 kg to about 0.21 kg. According to some embodiments, the amount of water in Step 4 is about 0.18 kg.

According to some embodiments, the amount of hydrochloric acid (HCl) in Step 4 ranges from about 0.009 kg to about 0.9 kg. According to some embodiments, the amount of hydrochloric acid (HCl) in Step 4 ranges from about 0.045 kg to about 0.45 kg. According to some embodiments, the amount of hydrochloric acid (HCl) in Step 4 ranges from about 0.018 kg to about 0.18 kg. According to some embodiments, the amount of hydrochloric acid (HCl) in Step 4 ranges from about 0.088 kg to about 0.092 kg. According to some embodiments, the amount of hydrochloric acid (HCl) in Step 4 ranges from about 0.07 kg to about 0.11 kg.

According to some embodiments, the amount of ethanolic hydrochloric acid in Step 4 ranges from about 0.13 kg to about 13 kg. According to some embodiments, the amount of ethanolic hydrochloric acid (HCl) in Step 4 ranges from about 0.65 kg to about 6.5 kg. According to some embodiments, the amount of ethanolic hydrochloric acid in Step 4 ranges from about According to some embodiments, the amount of ethanolic hydrochloric acid in Step 4 ranges from about 0.26 kg to about 2.6 kg. According to some embodiments, the amount of ethanolic hydrochloric acid in Step 4 ranges from about 1.274 kg to about 1.326 kg. According to some embodiments, the amount of ethanolic hydrochloric acid in Step 4 ranges from about 1.25 kg to about 1.35 kg. According to some embodiments, the amount of ethanolic hydrochloric acid in Step 4 is about 1.3 kg.

According to some embodiments, the theoretical yield of sarecycline hydrochloride (Formula I) is about 1.07 kg for every 1 kg of sarecycline free base (Formula VI). According to some embodiments, the observed yield of sarecycline hydrochloride (Formula I) ranges from about 70% to about 100% of the theoretical yield. According to some embodiments, the observed yield of sarecycline hydrochloride (Formula I) is about 95% of the theoretical yield. According to some embodiments, the observed yield of sarecycline hydrochloride (Formula I) ranges from about 0.749 kg to about 1.07 kg. According to some embodiments, the observed yield of sarecycline hydrochloride (Formula I) is about 1.017 kg.

According to some embodiments, the process for preparing sarecycline hydrochloride (Formula I) comprises an impurity. It is understood that impurities can be identified by analytical techniques well-known in the art. Such analytical techniques include, but are not limited to, titrimetric techniques, chromatographic techniques, spectroscopic techniques, electrochemical techniques, kinetic techniques, electrophoretic techniques, flow injection and sequential injection techniques and hyphenated techniques. Chromatographic techniques include, without limitation, thin layer chromatography (TLC), high performance thin layer chromatography (HPTLC), high-performance liquid chromatography (HPLC) and gas chromatography (GC). Exemplary spectroscopic techniques include, but are not limited to, spectrophotometry, near infrared spectroscopy (NIRS), nuclear magnetic resonance spectroscopy (NMR), fluorimetry and phosphorimetry. Electrochemical techniques include, but are not limited to, voltammetry, polarography, amperometry and potentiometry. Kinetic techniques include, without limitation, stopped flow system, continuous addition of reagent (CAR) technique, differential rate method, kinetic wavelength pair method and H-point standard addition method. Electrophoretic techniques, include, for example, capillary electrophoresis (CE). Capillary electrophoretic techniques include, without limitation, capillary zone electrophoresis, micellar electrokinetic chromatography, isotachophoresis, capillary gel electrophoresis, isoelectric focusing, and affinity capillary electrophoresis. Hyphenated techniques include, but are not limited to, liquid chromatography-mass spectrometry (LC-MS), gas chromatography-mass spectrometry (GC-MS), liquid chromatography-nuclear magnetic resonance spectroscopy (LC-NMR), liquid chromatography with tandem mass spectrometry (LC-MS/MS), liquid chromatography-electrospray ionization-mass spectrophotometry, capillary electrophoresis-inductively coupled plasma-mass spectrometry (CE-ICP-MS), capillary electrophoresis-mass spectrometry (CE-MS), HPLC with ultraviolet (UV) detection, HPLC with tandem mass spectrometry (HPLC-MS/MS) and the like.

According to some embodiments, the 7-iodosancycline trifluoroacetic acid salt (Formula III) intermediate comprises an impurity. Impurities include, but are not limited to, 7-bromosancycline, sancycline, 9-iodosancycline, 4R-epimer-9-iodosancycline, 4R-epimer-7-iodosancycline, anhydro-7, 9-bisiodosancycline, 4R-epimer-7, 9-bisiodosancycline and 7, 9-bisiodosancycline According to some embodiments, the impurity is 7-bromosancycline. According to some embodiments, the 7-iodosancycline trifluoroacetic acid salt (Formula III) intermediate comprises about ≤0.7% (area %) of 7-bromosancycline.

According to some embodiments, the impurity is sancycline. According to some embodiments, the 7-iodosancycline trifluoroacetic acid salt (Formula III) intermediate comprises about ≤2.0% (area %) of sancycline.

According to some embodiments, the impurity is 9-iodosancycline. According to some embodiments, the 7-iodosancycline trifluoroacetic acid salt (Formula III) intermediate comprises about ≤7.0% (area %) of 9-iodosancycline.

According to some embodiments, the impurity is 4R-epimer-9-iodosancycline. According to some embodiments, the 7-iodosancycline trifluoroacetic acid salt (Formula III) intermediate comprises about ≤2.0% (area %) of 4R-epimer-9-iodosancycline.

According to some embodiments, the impurity is 4R-epimer-7-iodosancycline. According to some embodiments, the 7-iodosancycline trifluoroacetic acid salt (Formula III) intermediate comprises about ≤4.0% (area %) of 4R-epimer-7-iodosancycline.

According to some embodiments, the impurity is anhydro-7, 9-bisiodosancycline. According to some embodiments, the 7-iodosancycline trifluoroacetic acid salt (Formula III) intermediate comprises about ≤1.0% (area %) of anhydro-7, 9-bisiodosancycline.

According to some embodiments, the impurity is 4R-epimer-7, 9-bisiodosancycline. According to some embodiments, the 7-iodosancycline trifluoroacetic acid salt (Formula III) intermediate comprises about ≤1.0% (area %) of 4R-epimer-7, 9-bisiodosancycline.

According to some embodiments, the impurity is 7, 9-bisiodosancycline. According to some embodiments, the 7-iodosancycline trifluoroacetic acid salt (Formula III) intermediate comprises about ≤2.1% (area %) of 7, 9-bisiodosancycline.

According to some embodiments, the purity of the 7-iodosancycline trifluoroacetic acid salt (Formula III) intermediate is about ≥84% (area %).

According to some embodiments, the Loss on Drying (LOD) of the 7-iodosancycline trifluoroacetic acid salt (Formula III) intermediate is about ≤7.0% (area %).

According to some embodiments, the 7-formylsancycline (Formula IV) intermediate comprises an impurity. Impurities include, but are not limited to, 4R-epimer-7-formylsancycline, 7, 9-bisformylsancycline, 9-formylsancycline, sancycline, anhydro-7, 9-bisformylsancycline and 7-iodosancycline.

According to some embodiments, the impurity is 4R-epimer-7-formylsancycline. According to some embodiments, the 7-formylsancycline (Formula IV) intermediate comprises about ≤7.3% (area %) of 4R-epimer-7-formylsancycline.

According to some embodiments, the impurity is 7, 9-bisformylsancycline. According to some embodiments, the 7-formylsancycline (Formula IV) intermediate comprises about ≤ 3.0% (area %) of 7, 9-bisformylsancycline.

According to some embodiments, the impurity is 9-formylsancycline. According to some embodiments, the 7-formylsancycline (Formula IV) intermediate comprises about ≤3.0% (area %) of 9-formylsancycline.

According to some embodiments, the impurity is sancycline. According to some embodiments, the 7-formylsancycline (Formula IV) intermediate comprises about ≤4.0% (area %) of sancycline.

According to some embodiments, the impurity is anhydro-7, 9-bisformylsancycline. According to some embodiments, the 7-formylsancycline (Formula IV) intermediate comprises about ≤0.5% (area %) of anhydro-7, 9-bisformylsancycline.

According to some embodiments, the impurity is 7-iodosancycline. According to some embodiments, the 7-formylsancycline (Formula IV) intermediate comprises about ≤0.7% (area %) of 7-iodosancycline.

According to some embodiments, the purity of the 7-formylsancycline (Formula IV) intermediate is about ≥85% (area %).

According to some embodiments, the Loss on Drying (LOD) of the 7-formylsancycline (Formula IV) intermediate is about ≤5.0% (area %).

According to some embodiments, the sarecycline free base (Formula VI) intermediate comprises an impurity. Impurities include, but are not limited to, sancycline, 12-hydroxysarecycline, 9-sarecycline, 7-formylsancycline, 7, 9-sarecycline, 4R-sarecycline, 7-methoxyiminomethylsancycline and sarecycline free base dimer.

According to some embodiments, the impurity is sancycline. According to some embodiments, the sarecycline free base (Formula VI) intermediate comprises about ≤1.0% (w/w %) of sancycline.

According to some embodiments, the impurity is 12-hydroxysarecycline. According to some embodiments, the sarecycline free base (Formula VI) intermediate comprises about ≤0.5% (w/w %) of 12-hydroxysarecycline.

According to some embodiments, the impurity is 9-sarecycline. According to some embodiments, the sarecycline free base (Formula VI) intermediate comprises about ≤0.75% (w/w %) of 9-sarecycline.

According to some embodiments, the impurity is 7-formylsancycline. According to some embodiments, the sarecycline free base (Formula VI) intermediate comprises about ≤1.0% (area %) of 7-formylsancycline.

According to some embodiments, the impurity is 7, 9-sarecycline. According to some embodiments, the sarecycline free base (Formula VI) intermediate comprises about ≤0.7% (w/w %) of 7, 9-sarecycline.

According to some embodiments, the impurity is 4R-sarecycline. According to some embodiments, the sarecycline free base (Formula VI) intermediate comprises about ≤1.5% (w/w %) of 4R-sarecycline.

According to some embodiments, the impurity is 7-methoxyiminomethylsancycline. According to some embodiments, the sarecycline free base (Formula VI) intermediate comprises about ≤0.55% (w/w %) of 7-methoxyiminomethylsancycline.

According to some embodiments, the impurity is sarecycline free base dimer. According to some embodiments, the sarecycline free base (Formula VI) intermediate comprises about ≤ 0.5% (w/w %) of sarecycline free base dimer.

According to some embodiments, the sarecycline free base (Formula VI) intermediate comprises ≤4.5% (w/w %) of total impurities.

According to some embodiments, the purity of the sarecycline free base (Formula VI) intermediate is about ≥95% (w/w %).

According to some embodiments, the Loss on Drying (LOD) of the sarecycline free base (Formula VI) intermediate is about ≤6.0% (w/w %).

According to some embodiments, the sarecycline hydrochloride (Formula I) comprises an impurity. Impurities include, but are not limited to, sancycline, 12-hydroxysarecycline, 9-sarecycline, 7-formylsancycline, 7, 9-sarecycline, 4R-sarecycline, 7-methoxyiminomethylsancycline and sarecycline free base dimer.

According to some embodiments, the impurity is sancycline. According to some embodiments, the sarecycline hydrochloride (Formula I) comprises about ≤1.0% (w/w %) of sancycline.

According to some embodiments, the impurity is 12-hydroxysarecycline. According to some embodiments, the sarecycline hydrochloride (Formula I) comprises about ≤0.5% (w/w %) of 12-hydroxysarecycline.

According to some embodiments, the impurity is 9-sarecycline. According to some embodiments, the sarecycline hydrochloride (Formula I) comprises about ≤1.0% (w/w %) of 9-sarecycline.

According to some embodiments, the impurity is 7-formylsancycline. According to some embodiments, the sarecycline hydrochloride (Formula I) comprises about ≤1.0% (area %) of 7-formylsancycline.

According to some embodiments, the impurity is 7, 9-sarecycline. According to some embodiments, the sarecycline hydrochloride (Formula I) comprises about ≤1.0% (w/w %) of 7, 9-sarecycline.

According to some embodiments, the impurity is 4R-sarecycline. According to some embodiments, the sarecycline hydrochloride (Formula I) comprises about ≤3.0% (w/w %) of 4R-sarecycline.

According to some embodiments, the impurity is 7-methoxyiminomethylsancycline. According to some embodiments, the sarecycline hydrochloride (Formula I) comprises about ≤ 1.0% (w/w %) of 7-methoxyiminomethylsancycline.

According to some embodiments, the impurity is sarecycline free base dimer. According to some embodiments, the sarecycline hydrochloride (Formula I) comprises about ≤0.5% (w/w %) of sarecycline free base dimer.

According to some embodiments, the sarecycline hydrochloride (Formula I) comprises ≤6.0% (w/w %) of total impurities.

According to some embodiments, the water content of the sarecycline hydrochloride (Formula I) is about ≤2.0% (w/w %).

According to some embodiments, the sarecycline hydrochloride (Formula I) comprises an elemental impurity. Elemental impurities include, but are not limited to, palladium, boron and chloride.

According to some embodiments, the elemental impurity is palladium. According to some embodiments, the sarecycline hydrochloride (Formula I) comprises ≤10 parts per million (ppm) of palladium.

According to some embodiments, the elemental impurity is boron. According to some embodiments, the sarecycline hydrochloride (Formula I) comprises ≤1,000 parts per million (ppm) of boron.

According to some embodiments, the elemental impurity is chloride. According to some embodiments, the sarecycline hydrochloride (Formula I) comprises from about 6.0% to about 8% (w/w %) of chloride. According to some embodiments, the sarecycline hydrochloride (Formula I) comprises from about 6.09% to about 7.45% (w/w %) of chloride.

According to some embodiments, the sarecycline hydrochloride (Formula I) comprises a residual solvent. Residual solvents include, but are not limited to, N-methylpyrrolidone, ethanol, t-butylmethyl ether, ethyl acetate, dichloromethane, propan-2-ol, acetone and methanol.

According to some embodiments, the residual solvent is N-methylpyrrolidone. According to some embodiments, the sarecycline hydrochloride (Formula I) comprises ≤50 parts per million (ppm) of N-methylpyrrolidone.

According to some embodiments, the residual solvent is ethanol. According to some embodiments, the sarecycline hydrochloride (Formula I) comprises ≤20,000 parts per million (ppm) of ethanol.

According to some embodiments, the residual solvent is t-butylmethyl ether. According to some embodiments, the sarecycline hydrochloride (Formula I) comprises ≤1,000 parts per million (ppm) of t-butylmethyl ether.

According to some embodiments, the residual solvent is ethyl acetate. According to some embodiments, the sarecycline hydrochloride (Formula I) comprises ≤1,000 parts per million (ppm) of ethyl acetate.

According to some embodiments, the residual solvent is dichloromethane. According to some embodiments, the sarecycline hydrochloride (Formula I) comprises ≤600 parts per million (ppm) of dichloromethane.

According to some embodiments, the residual solvent is propan-2-ol. According to some embodiments, the sarecycline hydrochloride (Formula I) comprises ≤1,000 parts per million (ppm) of propan-2-ol.

According to some embodiments, the residual solvent is acetone. According to some embodiments, the sarecycline hydrochloride (Formula I) comprises ≤1,000 parts per million (ppm) of acetone.

According to some embodiments, the residual solvent is methanol. According to some embodiments, the sarecycline hydrochloride (Formula I) comprises ≤1,000 parts per million (ppm) of methanol.

According to some embodiments, the purity of the sarecycline hydrochloride (Formula I) is about ≥95% (w/w %).

According to some embodiments, stoichiometric amounts of raw materials used in the process for preparing sarecycline hydrochloride (Formula I) can be proportionally scaled. By way of example, raw materials include, but are not limited to, starting materials, reagents, solvents and catalysts.

According to some embodiments, the water used in the process for preparing sarecycline hydrochloride (Formula I) is potable. According to some embodiments, the water used in the process for preparing sarecycline hydrochloride (Formula I) is purified. Types of purification include, but are not limited to, distillation, deionization, reverse osmosis, double pass reverse osmosis and carbon filtration. According to some embodiments, the water used in the process for preparing sarecycline hydrochloride (Formula I) is sterile. Types of sterilization include, but are not limited to, non-chemical and chemical methods. Non-limiting examples of non-chemical methods include ultraviolet (UV) light, heat and filtration. Non-limiting examples of chemical methods include ozone and chlorine or chlorine compounds. Examples of chlorine compounds include, but are not limited to, chloramine, chlorine dioxide, sodium hypochlorite, calcium hypochlorite and the like.

According to some embodiments, an individual component of the process for preparing sarecycline hydrochloride (Formula I) can be identified by a suitable analytical method.

According to some embodiments, an individual component of the process for preparing sarecycline hydrochloride (Formula I) can be quantified by a suitable analytical method. According to some embodiments, an individual component of the process for preparing sarecycline hydrochloride (Formula I) can be isolated by a suitable analytical method. According to some embodiments, an individual component of the process for preparing sarecycline hydrochloride (Formula I) can be purified by a suitable analytical method. Such suitable analytical methods include, but are not limited to, chromatography, spectroscopy, nuclear magnetic resonance (NMR) and mix melting point. Exemplary chromatography methods include, without limitation, column chromatography, ion-exchange chromatography, gel-permeation (molecular sieve) chromatography, affinity chromatography, paper chromatography, thin-layer chromatography, gas chromatography, dye-ligand chromatography, hydrophobic interaction chromatography, pseudoaffinity chromatography and high-performance liquid chromatography (HPLC). Spectroscopy methods include, but are not limited to, X-ray spectroscopy, atomic emission (AE) spectroscopy, atomic absorption (AA) spectroscopy, spark or arc (emission) spectroscopy, visible/ultraviolet (UV) spectroscopy, mass spectroscopy, infrared (IR) spectroscopy and near infrared (NIR) spectroscopy. Exemplary NMR methods include, without limitation, hydrogen (1H) NMR and carbon (13C) NMR.

According to some embodiments, the moisture content of an individual component of the process for preparing sarecycline hydrochloride (Formula I) can be determined. Methods suitable for determining moisture content include, but are not limited to, Karl Fischer (KF) titration and Loss on Drying (LOD). Karl Fischer titration includes, but is not limited to, volumetric and coulometric.

Karl Fischer titration is a moisture determination method specific for water. The method involves a chemical analysis procedure which is based on the oxidation of sulfur dioxide by iodine in a methanolic hydroxide solution:

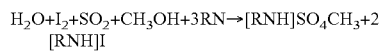
$$H_2O+I_2+SO_2+CH_3OH+3RN \rightarrow [RNH]SO_4CH_3+2[RNH]I$$

The titration can be performed volumetrically or coulometrically. In the volumetric method, a Karl Fischer solution containing iodine is added until the first trace of excess iodine is present. The amount of iodine converted is determined from the burette volume of the iodine-containing Karl Fischer solution. In the coulometric procedure, the iodine participating in the reaction is generated directly in the titration cell by electrochemical oxidation of iodide until a trace amount of unreacted iodine is detected.

Loss on Drying (LOD) is a method used to determine the moisture content of a sample or the loss of any volatile matter from a sample. The method can be performed by taring an appropriate glass-stoppered, shallow weighing bottle that has been dried for about 30 minutes under the same conditions to be employed in the LOD determination and cooled to room temperature in a desiccator. The sample is then placed in the bottle, the cover is replaced and the bottle and the contents (i.e., sample) are weighed. After weighing, the sample is distributed by gentle, sidewise shaking, as evenly as practicable. The stopper is removed from the bottle and the stopper and the bottle are placed in a drying chamber. After drying, the chamber is opened and the bottle is promptly closed and allowed to come to room temperature in a desiccator before weighing (See, e.g., U.S. Pharmacopeia, <731> LOSS ON DRYING). The difference in weight measured before and after drying is taken as the percentage of moisture in the sample.

According to some embodiments, the process for preparing sarecycline hydrochloride (Formula I) is performed in a commercially-available reactor. Reactors include, but are not limited to, stainless steel, hastelloy and glass-lined.

Unless defined otherwise, all technical and scientific terms used herein have the same meaning as commonly understood by one of ordinary skill in the art to which this invention belongs. Although any methods and materials similar or equivalent to those described herein also can be used in the practice or testing of the described invention, the preferred methods and materials are now described.

All publications mentioned herein are incorporated by reference to disclose and describe the methods and/or materials in connection with which the publications are cited.

The publications discussed herein are provided solely for their disclosure prior to the filing date of the present application. Nothing herein is to be construed as an admission that the described invention is not entitled to antedate such publication by virtue of prior invention. Further, the dates of publication provided may be different from the actual publication dates which may need to be independently confirmed.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

It must be noted that as used herein and in the appended claims, the singular forms "a", "an", and "the" include plural references unless the context clearly dictates otherwise.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Process for Preparing Sarecycline Hydrochloride-Scheme 1

Step 1

One kilogram (1 kg) of sancycline ((4S, 4aS, 5aR, 12aR)-4-(dimethylamino)-1, 10, 11, 12a-tetrahydroxy-3, 12-dioxo-4a, 5, 5a, 6-tetrahydro-4H-tetracene-2-carboxamide) was mixed with 8.25 kg of trifluoroacetic acid (TFA), the mixture was stirred at ambient temperature under nitrogen atmosphere until dissolved and the resulting solution was cooled to 0° C. Next, 0.625 kg of N-iodosuccinimide (NIS) was added to the solution. The solution containing NIS was heated to 25° C. and stirred until the reaction was completed as determined by HPLC. Next, the TFA was distilled, the resulting residue was cooled to 15-20° C. and product was precipitated by slowly adding approximately 1 kg of isopropanol followed by the addition of approximately 9 kg of tetrahydrofuran (THF). The precipitated product was then cooled to −8° C. and held at that temperature for 2-8 hours. Finally, the precipitated product was filtered, washed with cold THF, and dried at no more than 30° C.

This step yielded approximately 0.98 kg of 7-iodosancycline for every 1 kg of sancycline charged.

Step 2

A suspension of 0.34 kg of sodium carbonate ($NaCO_3$), 0.13 kg of cellulose or $SiO_2$ and 2.25 kg of N-methyl pyrrolidone (NMF) was stirred at ambient temperature under nitrogen atmosphere until the oxygen content reached 1000 parts per billion (ppb). Next, 0.0080 kg of triphenylphosphine ($PPh_3$), 1 kg of 7-Iodosancycline and 0.26% of Bis-(Triphenyl Phosphine) palladium chloride (BTPP—$PdCl_2$) was added to the suspension while maintaining a low oxygen content. 0.22 kg of triethylsilane ($Et_3SiH$) was added to the suspension while carbon monoxide (CO) was bubbled through the suspension to reach a pressure of 5 bar CO. The suspension was gradually heated to 75° C. until the reaction was complete as determined by HPLC. Next, the suspension was filtered hot and mother liquors were mixed with 0.13 kg of cellulose or $SiO_2$. 5.80 kg of water was added to the suspension while maintaining a temperature of 45° C. under stirring. The suspension was filtered and mother liquors were cooled to ambient temperature. Next, the pH of the solution was adjusted to 7.4 under stirring, followed by the addition of 2 kg of ethanol (EtOH). The suspension was stirred for an additional 2-8 hours, filtered, and washed with EtOH and water to obtain a wet cake. Water was added to the wet cake and stirred for 2-8 hours to produce a slurry. The slurry was filtered, washed with water, washed with EtOH and dried at no more than 50° C.

This step yielded approximately 0.50 kg of 7-formylsancycline for every 1 kg of 7-iodosancycline charged.

Step 3a

One kilogram (1 kg) of 7-formylsancycline was mixed with a solution of 0.50 kg of dimethylhydroxylamine (DMHA) free base in 2.8 kg of methanol (MeOH) and the resulting mixture was cooled to −9° C. Next, 1 kg of oxalic acid and 0.180 kg of dimethylaminoborane (DMAB) was added to the mixture at −9° C. and the mixture was stirred while maintaining a temperature of −9° C. until the reaction reached completion as confirmed by in-process HPLC analysis. An additional 0.40 kg of oxalic acid was added to the mixture and the mixture was stirred for an additional hour. The excess DMAB was quenched by the addition of 2.2 kg of acetone and the mixture was stirred for 2-8 hours. After stirring, the mixture was filtered to produce a wet cake. The wet cake was then washed with >2.4 kg of cold acetone and immediately used in the next process step (step 3b).

Step 3b

One kilogram (1 kg) of crude oxalate salt, 0.27 kg of cellulose or $SiO_2$ and >9 kg of dichloromethane (DCM) were mixed with the wet cake from step 3a at ambient conditions and the pH of the resulting suspension was adjusted to 8.1. Next, >8 kg of water and 0.55 kg of methanol (MeOH) were added to the suspension and the suspension was stirred. After stirring, the suspension was filtered to produce a wet cake. The wet cake was washed with 2.3 kg of DCM, the pH was adjusted to 7.9 and the resulting solution was heated to about 30° C. under stirring and allowed to stand for phase separation. After phase separation, the aqueous phase was extracted and organic fractions were combined. The combined organic fraction was then concentrated under vacuum, mixed with >3 kg of acetone and distilled under vacuum. This solvent exchange process was repeated 3 times and the resulting residue was dissolved in >3.2 kg of acetone and >0.8 kg of water at 20° C. under stirring. The dissolved residue was gradually cooled to 0° C. to produce a crystallized product. The crystallized product was then filtered, washed with cold acetone and dried under vacuum at no more than 30° C. This step yielded approximately 0.66 kg of sarecycline free base for every 1 kg of 7-formylsancycline charged.

Step 4

One kilogram (1 kg) of sarecycline free base, 14.3 kg of ethanol (EtOH) and 0.18 kg of water were mixed and stirred at ambient temperature. Next, ethanolic aqueous HCl solution was added to the mixture at ambient conditions. The mixture was then gradually cooled to 0° C. under low stirring for 2-8 hours and filtered to produce a wet cake. The wet cake was washed with cold ethanol and dried below 40° C.

This step yielded approximately 1 kg of sarecycline hydrochloride for every 1 kg of sarecycline free base charged.

Example 2: Process for Preparing Sarecycline Hydrochloride-Scheme 2

Step 1

8.0-8.5 kg of trifluoracetic acid (TFA) was charged to a suitable nitrogen purged reactor at 15° C.±5° C. While maintaining the temperature at 15° C.±5° C., 0.98-1.02 kg (2.36-2.46 moles) of sancycline ((4S, 4aS, 5aR, 12aR)-4-(dimethylamino)-1, 10, 11, 12a-tetrahydroxy-3, 12-dioxo-4a, 5, 5a, 6-tetrahydro-4H-tetracene-2-carboxamide) was added. Once complete dissolution of sancycline was visually verified, the solution was cooled to 5° C.±5° C. Next, 0.60-0.65 kg (2.83-3.05 moles) of N-iodosuccinimide (NIS) was added and the solution was stirred for about 1 hour. The solution was gradually heated to 17° C.-23° C. and stirred until the reaction completion was verified by HPLC (≤4.0% (area %)). Next, the TFA was distilled under vacuum, below a temperature of 28° C. Once distillation was complete, the residue was cooled to 15° C.-20° C. and >0.9 kg of isopropyl alcohol was added under stirring. Next, >10 kg of tetrahydrofuran (THF) was slowly added to the solution while maintaining the temperature between 10° C.-20° C. The solution was then stirred at 10° C.-20° C. until the formation of a precipitate was visually observed. The solution was cooled to −8° C. to −5° C. and held at that temperature for 2 to 8 hours to form a precipitated product. The precipitated product was filtered and washed with pre-cooled (−5° C. to 0° C.) THF. The resulting wet product was dried at no more than 30° C. under vacuum until a loss on drying (LOD) limit of ≤7.0% w/w was reached.

This step yielded approximately 0.60-1.51 kg of 7-iodosancycline for every 1 kg of sancycline charged.

Step 2

0.32-0.36 kg of sodium carbonate, 0.12-0.15 kg of cellulose or $SiO_2$ and 2.10-2.45 kg of N-methyl pyrrolidone (NMP) were charged to a suitable nitrogen purged reactor (R1) and the resulting suspension was stirred at 25° C.±5° C. R1 was purged with nitrogen until the oxygen content was no more than 1000 ppb. Next, R1 was charged with 0.0075-0.0085 kg triphenylphosphine ($PPh_3$), followed by 0.98-1.02 kg (1.50 to 1.56 moles) 7-Iodosancycline, while maintaining the temperature at 25° C.±5° C. Next, 0.0022-0.0034 kg Bis-(Triphenyl Phosphine) palladium chloride catalyst (BTPP—PdCl2; 0.26%+0.05%, mol/mol) was added to R1 while maintaining an oxygen content of less than 1000 ppb. The contents of R1 were then transferred to another clean reactor (R2) at 25° C.±5° C. under vacuum. The oxygen content of R2 was controlled to less than 1000 ppb. 0.20-0.24 kg (1.72 to 2.06 moles) of triethylsilane ($Et_3SiH$) was added to R2 and the reactor was pressurized with carbon monoxide (CO) to about 5±0.5 bar. The suspension was then slowly heated to about 75° C.±5° C. and stirred until the reaction was complete as determined by HPLC (≤0.8% (area %)). Upon reaction completion, the solution was filtered hot into another clean reactor (R3). 0.13-0.15 kg cellulose or $SiO_2$ was then charged to R3 and the temperature was adjusted under stirring to 45° C.±5° C. Next, while maintaining the temperature at 45° C.±5° C., 5.75-5.85 kg purified water was charged to R3 and the solution was stirred and subsequently filtered. The filtered solution was then cooled to 20° C.±5° C. and a solution of about 50% sulfuric acid ($H_2SO_4$) was added until a pH value of 7.4±0.2 was reached. The solution was stirred while 1.95-2.0 kg of ethanol (EtOH) was added. Stirring continued at 20° C.±5° C. for a minimum of 2 hours. After stirring, the solution was filtered and the product was washed with 0.75-0.85 kg of EtOH followed by 0.95-1.05 kg of purified water. The resulting wet product was slurried with 5.7-5.8 kg of purified water and stirred at 20° C.-25° C. Next, the slurry was filtered to produce a cake. R3 and the cake were then washed with 0.90-1.10 kg purified water. Next, the cake was rinsed with 0.55-0.65 kg EtOH and dried at no more than 50° C. until a loss on drying (LOD) of ≤5% was reached.

This step yielded approximately 0.402-0.536 kg of 7-formylsancycline for every 1 kg of 7-iodosancycline charged.

Step 3a 0.98-1.02 kg (2.21 to 2.30 moles) of 7-formylsancycline, a cold (2° C. to 8° C.) solution of 0.49-0.52 kg (8.133 to 8.48 moles) dimethylhydroxylamine (DMHA) free base (prepared by dissolving 1 kg±0.05 kg of DMHA HCl in 3.20 kg±0.05 kg of methanol and 1.70-1.80 kg of 30% sodium methoxide solution in methanol) and 2.75-2.85 kg methanol (MeOH) were charged to a suitable nitrogen purged reactor, and the mixture was cooled to −5° C. to −14° C. to obtain a dark green suspension. A solution of 10.55-11.00 moles oxalic acid (prepared by dissolving 0.95 kg to 1.0 kg of anhydrous oxalic acid in 1.1 kg to 1.2 kg methanol) was slowly added to the suspension under stirring while maintaining the temperature between −5° C. to −14° C. Next, 2.97-3.14 moles dimethylaminoborane (DMAB) solution (prepared by dissolving 0.175-0.185 kg of DMAB in 1.1-1.2 kg methanol) was added to the solution while maintaining the same internal temperature (−5° C. to −14° C.). The contents were stirred at −5° C. to −14° C. until the reaction was complete as determined by HPLC (not more than 1.7% (% area)). While maintaining the temperature below 0° C., 0.35-0.45 kg oxalic acid anhydrous solid was added to the suspension and the suspension was stirred for approximately 1 hour at 0° C.±5° C. Next, >2.2. kg volume of acetone was slowly added while maintaining an internal temperature of 0° C.±5° C. to quench the reaction. The suspension was stirred for a minimum of 2 hours and then filtered to produce a cake. The reactor and the cake were then washed with >2.4 kg of cold acetone before immediately using the wet cake in the next step of the process (step 3b) or storing the wet cake at 2° C.-8° C. for ≤3 days.

Step 3b

The crude oxalate from step 3a was charged to a suitable reactor. While maintaining the temperature between 15° C.-25° C., 0.26-0.29 kg of cellulose and >9 kg of dichloromethane (DCM) were also charged to the reactor and the pH of the resulting suspension was adjusted to 8.1±0.2 with 28% ammonium hydroxide ($NH_3$ (aq.)) and/or 36% hydrochloric acid (HCl). Next, >8 kg of purified water and 0.37-0.75 kg of methanol were charged to the reactor and the suspension was stirred. The resulting product mass was then filtered and the cake was washed with 1.8-2.7 kg dichloromethane. The pH of the resulting solution was adjusted to 7.9±0.2. The solution was heated to 30° C.±5° C. under stirring and allowed to stand for phase separation. The organic phase was collected in a suitable reactor and the aqueous phase was extracted with dichloromethane and was separated. The combined organic phase was washed with >5 kg of water and the aqueous phase was again extracted with dichloromethane (>1 kg) and separated. The combined organic phase was distilled under vacuum without exceeding an internal temperature of 20° C.±5° C., filtered, washed with dichloromethane, and concentrated. The concentrated organic layer was mixed with >3 kg of acetone and distilled under vacuum at 20° C.±5° C. This solvent exchange procedure was repeated using an equivalent quantity of acetone for total of 3 times. After distillation, >3.2 kg of acetone and >0.8 kg of purified water were charged to the residue under stirring at 20±5° C. The solution was then gradually cooled to 0° C.±5° C. and slowly stirred until a crystallized product was formed. The crystallized product was then filtered and washed 2 times with pre-cooled acetone (about 0.75 kg). The resulting wet cake was dried under vacuum at a temperature of not more than 30° C. until an LOD of $6.0% was reached.

This step yielded approximately 0.385-0.748 kg of sarecycline free base for every 1 kg of 7-formylsancycline charged.

Step 4

0.98-1.02 kg of sarecycline free base, 14.0-14.6 kg EtOH and 0.15-0.21 kg of purified water were charged to a suitable nitrogen purged reactor (R1) and stirred at 20° C.±5° C. To a separate reactor (R2), 0.29-0.35 kg EtOH was charged and cooled to −5° C.±3° C. Next, 36% hydrochloric acid (HCl) (about 0.07-0.11 kg) was added to R2 under stirring. The above precooled ethanolic hydrochloric acid solution from R2 was transferred to R1 under stirring at 20° C.±5° C. Additional precooled ethanolic hydrochloric acid solution (about 1.25 kg to 1.35 kg; prepared by dissolving 0.28-0.30 kg of 36% HCl in 0.61-1.21 kg of ethanol) was slowly charged to R1 while maintaining the temperature at 20° C.±5° C. Next, the solution was gradually cooled to 0° C.±5° C. under slow stirring. Once the temperature of 0° C.±5° C. was reached, stirring was maintained at 0° C.±5° C. for a minimum of 2 hours. The solution was then filtered to produce a wet cake. The wet cake was washed with precooled ethanol (≥3 kg), and dried under vacuum at not more than 40° C. until LOD of ≤1.7% and water content of ≤1.0% as determined by Karl Fischer titration were reached.

This step yielded approximately 0.7-1 kg of sarecycline hydrochloride for every 1 kg of sarecycline free base charged.

Example 3: Reworking Procedure for Step 3b of the Process for Preparing Sarecycline Hydrochloride The following procedure was implemented when sarecycline free base (step 3b intermediate) failed to meet an intermediate release purity specification of ≥98% and/or impurities such as 7-formylsarecycline (>1.0%), 7-methoxy-iminomethyl (>1.0%) and Sancycline (>1.0%) were detected.

About 3.50-3.80 kg trifluoroacetic acid was charged to a suitable reactor at 10° C.-20° C. Sarecycline free base batch (about 1 kg±0.5 kg) was then added to the reactor, followed by 0.95-1.05 kg water and stirred at 20° C.-25° C. for 4-6 hours. To the reactor is then added About 0.98-1.2 kg isopropanol and about 8.5-9 kg tetrahydrofuran were added to the reactor at 20° C.-25° C. and stirred for a minimum of 2 hrs. The mixture was then cooled to 0° C.-5° C., stirred for at least 1 hour and filtered to produce a wet cake. The wet cake was then washed 2 times with pre-cooled (0° C. to 5° C.) tetrahydrofuran (about 1.2 kg to 1.5 kg) and crude oxalate salt wet cake was isolated. The crude oxalate salt wet cake was then transferred to another reactor and step 3b (above) was followed using equivalent amounts of reagents and solvents based on the input amount of crude oxalate salt.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A process for preparing sarecycline hydrochloride of Formula (I)

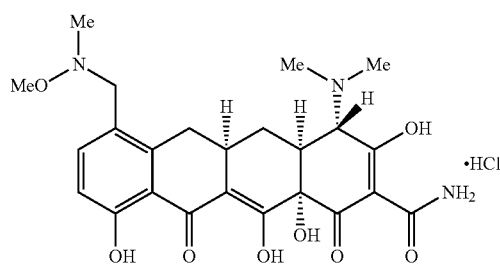

(I)

comprising:
(a) reacting (4S,4aS,5aR,12aR)-4-(dimethylamino)-1,10,11,12a-tetrahydroxy-3, 12-dioxo-4a,5,5a,6-tetra-hydro-4H-tetracene-2-carboxamide of Formula II

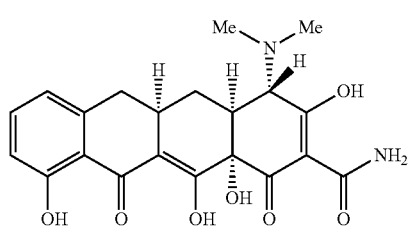

(II)

with
(i) trifluoroacetic acid (TFA); and
(ii) N-iodosuccinimide (NIS);

to form 7-iodosancycline trifluoroacetic acid salt of Formula III

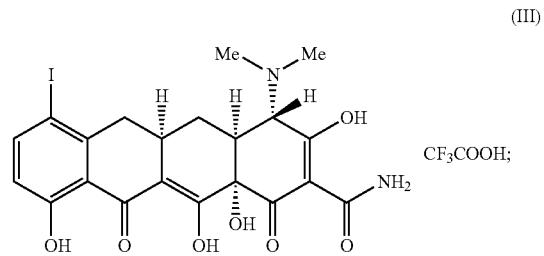

(III)

b) reacting the 7-iodosancycline trifluoroacetic acid salt of Formula (III) with
(i) N-methyl pyrrolidone (NMP);
(ii) triphenylphosphine (PPh$_3$);
(iii) Bis-(Triphenyl Phosphine) palladium chloride catalyst (BTPP—PdCl$_2$);
(iv) triethylsilane (Et$_3$SiH); and
(v) carbon monoxide (CO);
to form 7-formylsancycline of Formula IV

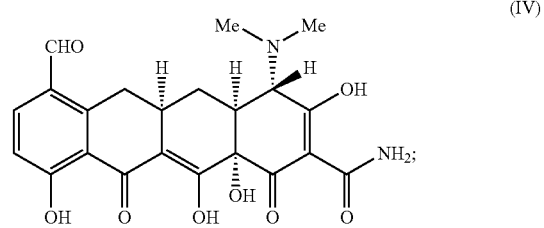 [SMILES: CN(C)[C@@H]1C(O)=C(C(N)=O)C(=O)[C@@]2(O)C(O)=C3C(=O)c4c(O)ccc(C=O)c4C[C@H]3C[C@@H]12]

(IV)

c) reacting the 7-formylsancycline of Formula IV with
(i) dimethylhydroxylamine (DMHA) free base;
(ii) oxalic acid;
(iii) dimethylaminoborane (DMAB); and
(iv) acetone
to form sarecycline crude oxalate salt of Formula V

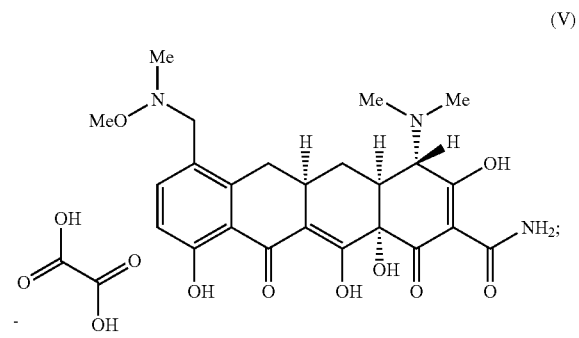

(V)

d) reacting the sarecycline crude oxalate salt of Formula V with
  (i) ammonium hydroxide (NH₃ (aqueous)) or hydrochloride acid (HCl);
  to form sarecycline free base of Formula VI

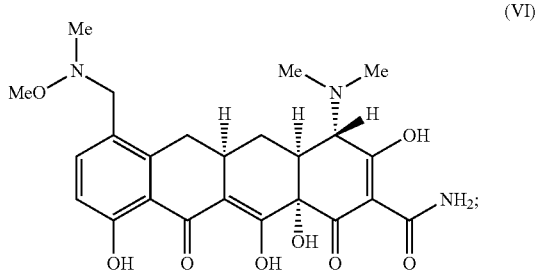 [SMILES: CON(C)Cc1ccc(O)c2c1C[C@H]1C[C@H]3[C@H](N(C)C)C(O)=C(C(N)=O)C(=O)[C@@]3(O)C(O)=C1C2=O]

(e) reacting the sarecycline free base of Formula VI with
  (i) ethanolic hydrochloric acid solution
  to form the sarecycline hydrochloride of Formula I.

2. The process according to claim 1, wherein step (a) further comprises
  i. isopropanol; or
  ii. tetrahydrofuran (THF); or
  iii. isopropanol and tetrahydrofuran (THF).

3. The process according to claim 1, wherein step (b) further comprises
  i. cellulose or SiO₂; or
  ii. sodium carbonate (Na₂CO₃); or
  iii. water; or
  iv. sulfuric acid (H₂SO₄); or
  v. ethanol (EtOH); or
  vi. a combination thereof.

4. The process according to claim 1, wherein step (c) further comprises methanol (MeOH).

5. The process according to claim 1, wherein step (d) further comprises
  i. cellulose or SiO₂; or
  ii. dichloromethane (DCM); or
  iii. water; or
  iv. methanol (MeOH); or
  v. acetone; or
  vi. a combination thereof.

6. The process according to claim 1, wherein step (e) further comprises
  i. ethanol (EtOH); or
  ii. water; or
  iii. hydrochloric acid (HCl); or
  iv. a combination thereof.

7. The process according to claim 1, wherein step (d) is repeated at least one time.

8. The process according to claim 1, further comprising:
  (d') reacting the sarecycline free base of Formula VI with
    (i) trifluoroacetic acid (TFA); and
    (ii) tetrahydrofuran (THF)
  and repeating steps (d) and (e).

9. The process according to claim 8, wherein step (d') further comprises
  i. water; or
  ii. isopropanol; or
  iii. water and isopropanol.

10. The process according to claim 8, wherein steps (d') and (d) are repeated at least one time.

* * * * *

UNITED STATES PATENT AND TRADEMARK OFFICE
CERTIFICATE OF CORRECTION

PATENT NO. : 12,297,161 B2
APPLICATION NO. : 17/043017
DATED : May 13, 2025
INVENTOR(S) : Palombi et al.

It is certified that error appears in the above-identified patent and that said Letters Patent is hereby corrected as shown below:

In the Specification

Column 19, Lines 1-15:

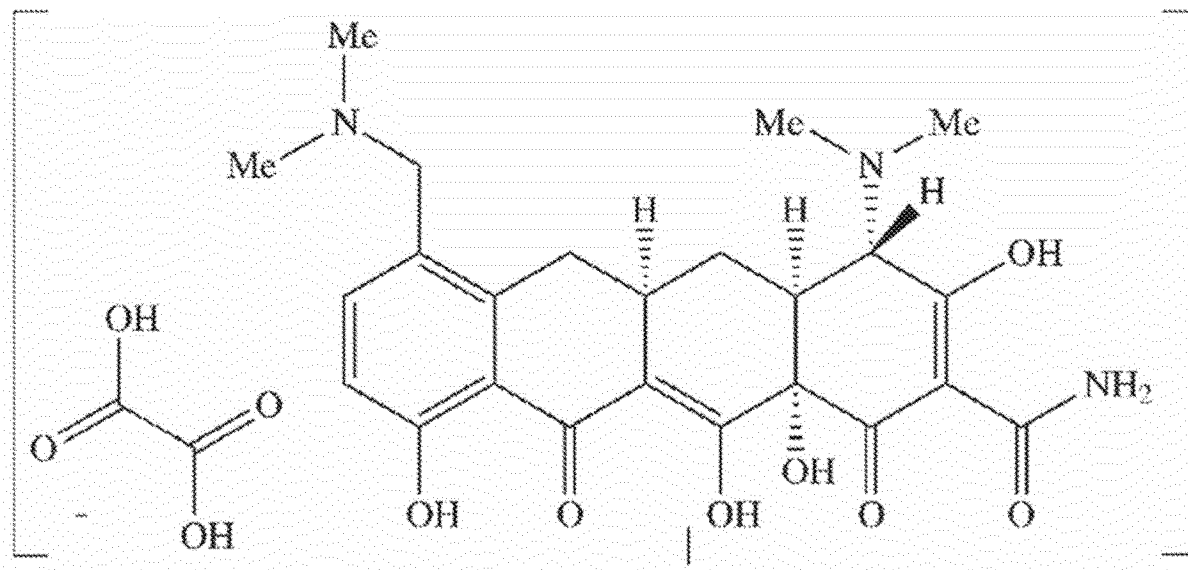

Should read as:

Signed and Sealed this
Second Day of September, 2025

Coke Morgan Stewart
*Acting Director of the United States Patent and Trademark Office*

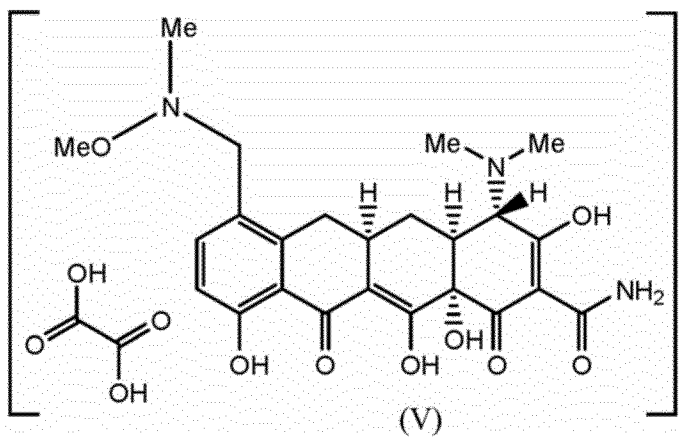
Column 19-20, Lines 23-39:
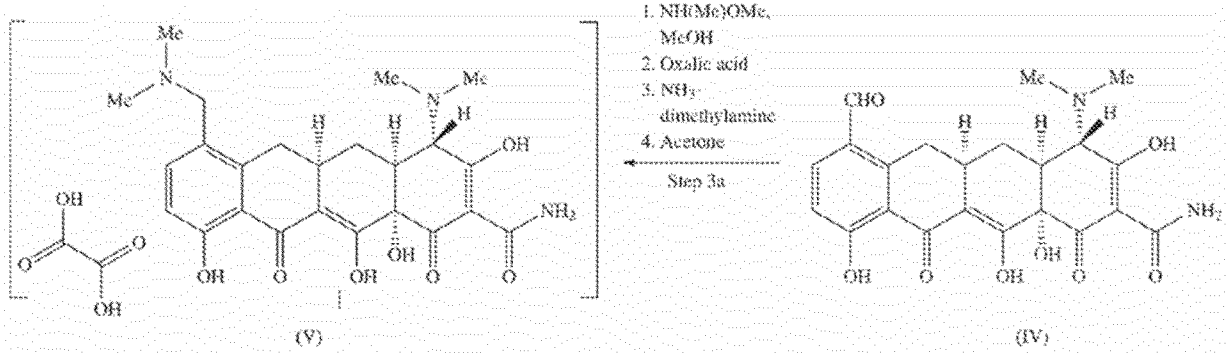
Should read as:
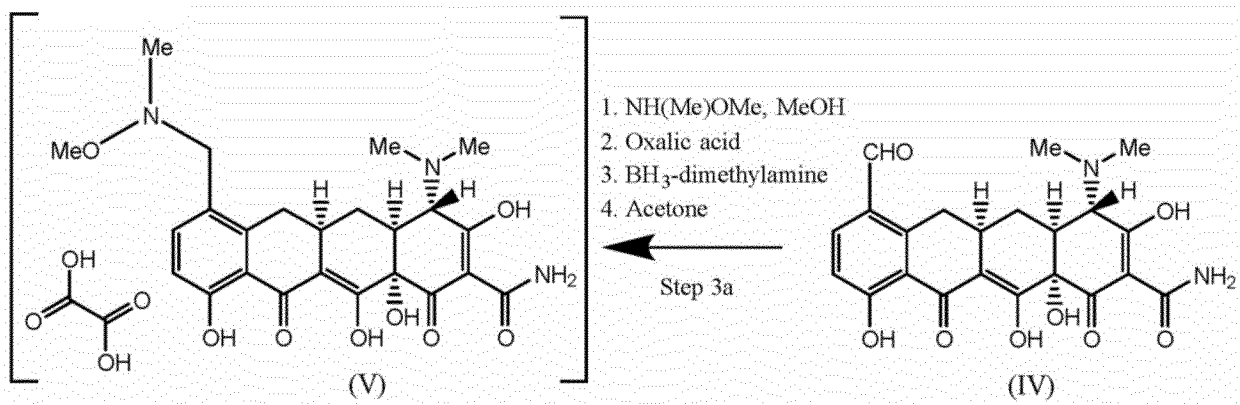
Column 21, Lines 37-50:

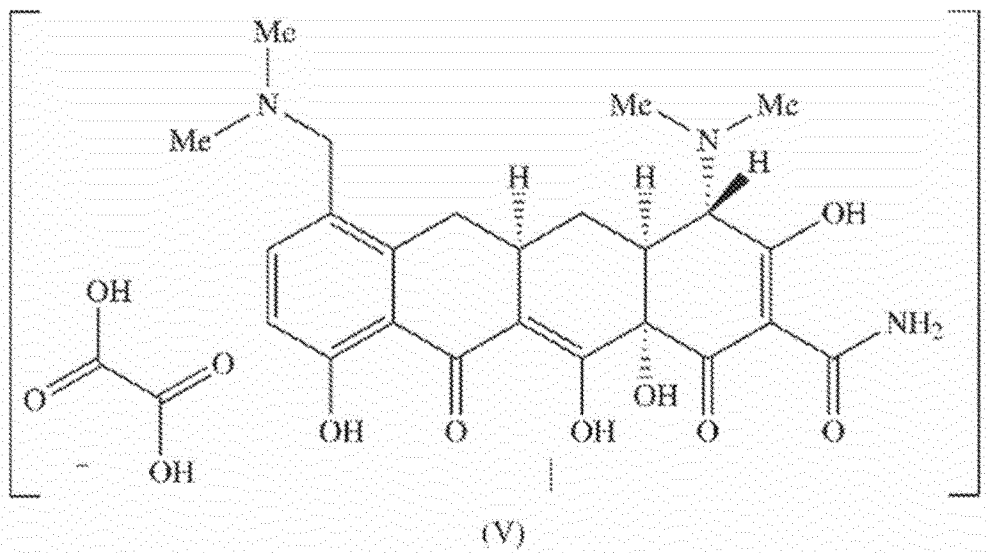
Should read as:
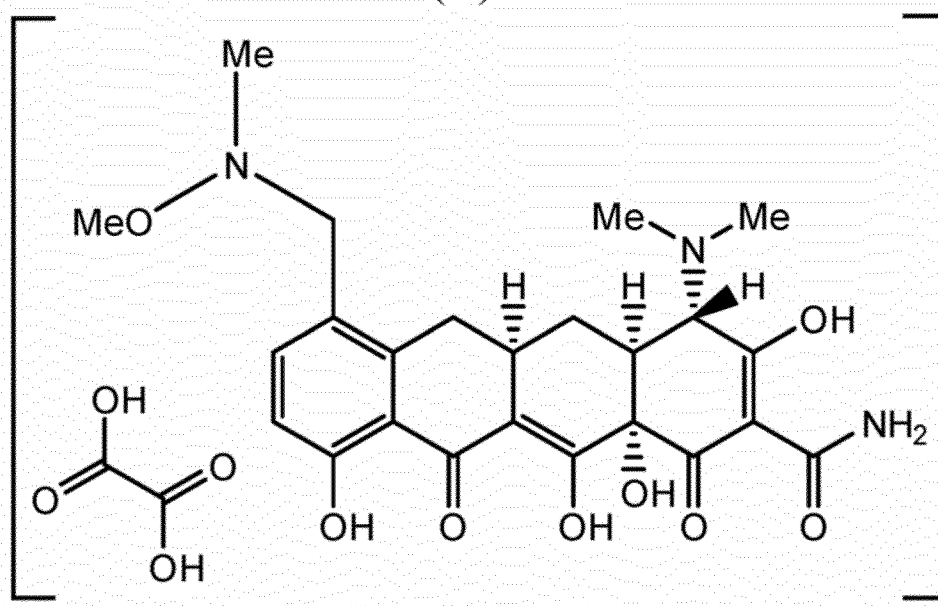
Column 22, Lines 8-20:

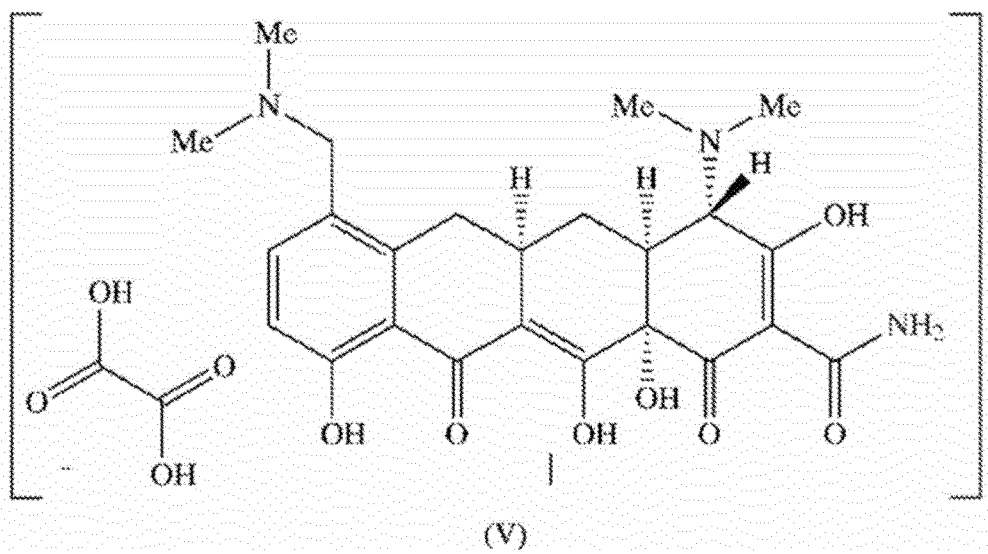
Should read as:
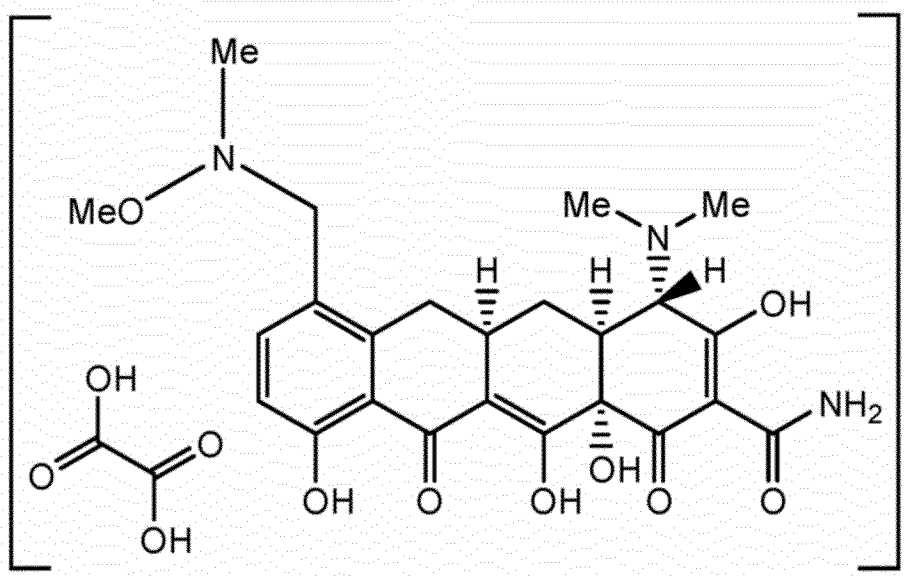
Column 22, Lines 45-65:

CERTIFICATE OF CORRECTION (continued)
U.S. Pat. No. 12,297,161 B2

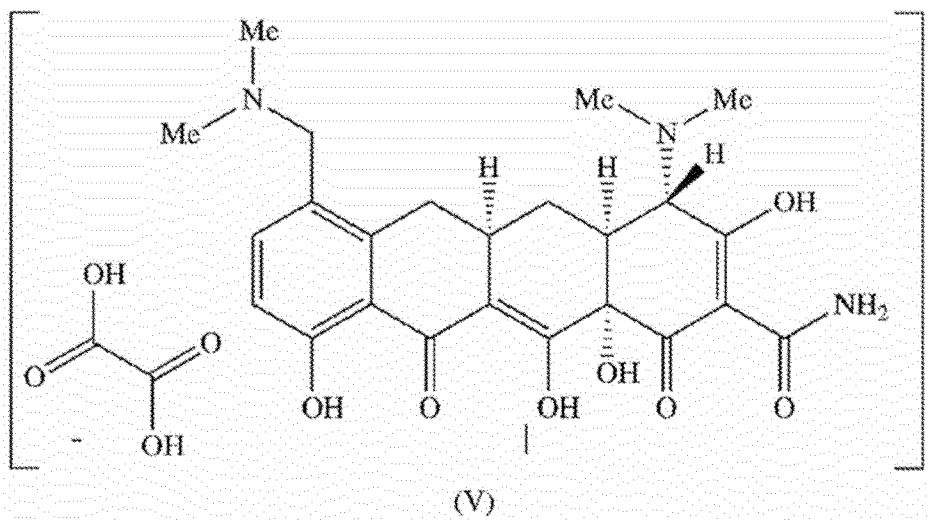

Should read as:

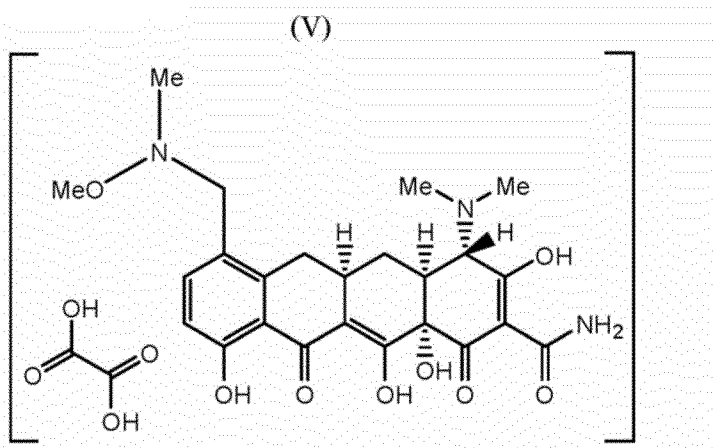

Column 23, Lines 25-45:

CERTIFICATE OF CORRECTION (continued)
U.S. Pat. No. 12,297,161 B2

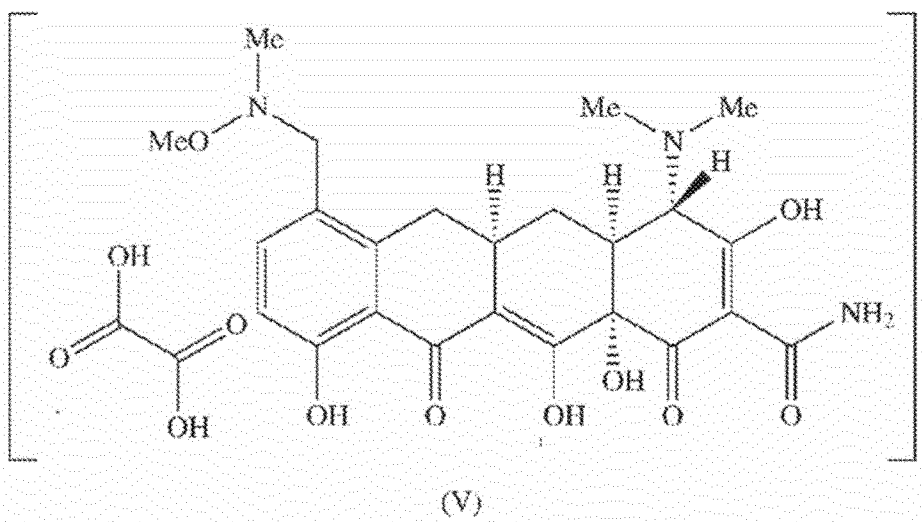

Should read as:

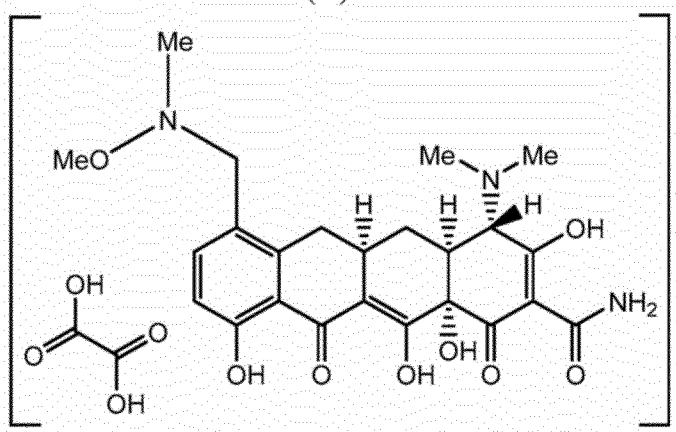

Column 24, Lines 1-19:

CERTIFICATE OF CORRECTION (continued)
U.S. Pat. No. 12,297,161 B2

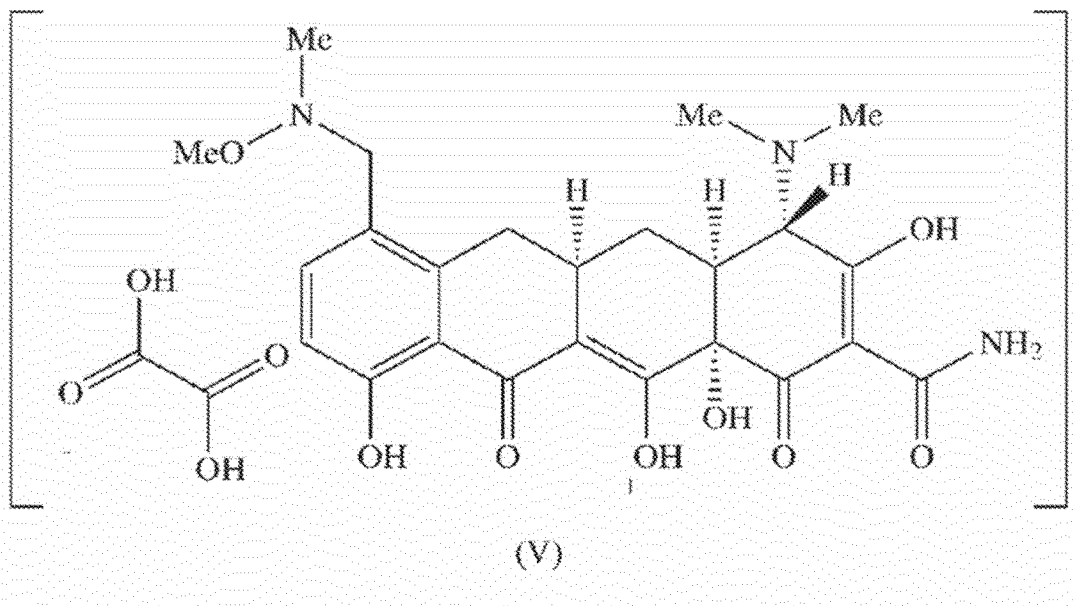

(V)

Step 3b
1. aq. NH$_3$, or HCl, DCM, water
2. cellulose or SiO$_2$, MeOH
3. acetone, water Should read as:

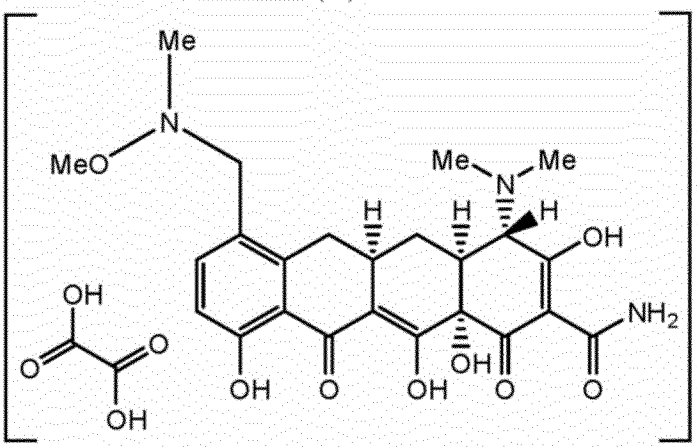

(V)

Step 3b
1. aq. NH$_3$, HCl, DCM, water
2. cellulose or SiO$_2$, MeOH
3. acetone, water Column 27, Lines 37-49:

CERTIFICATE OF CORRECTION (continued)
U.S. Pat. No. 12,297,161 B2

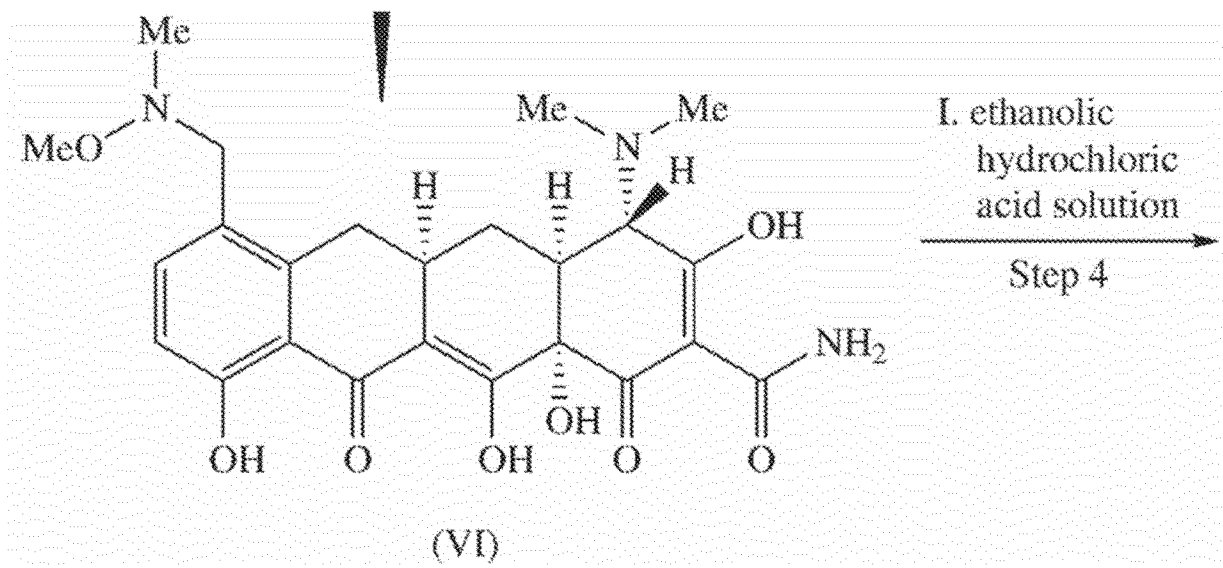

Should read as:

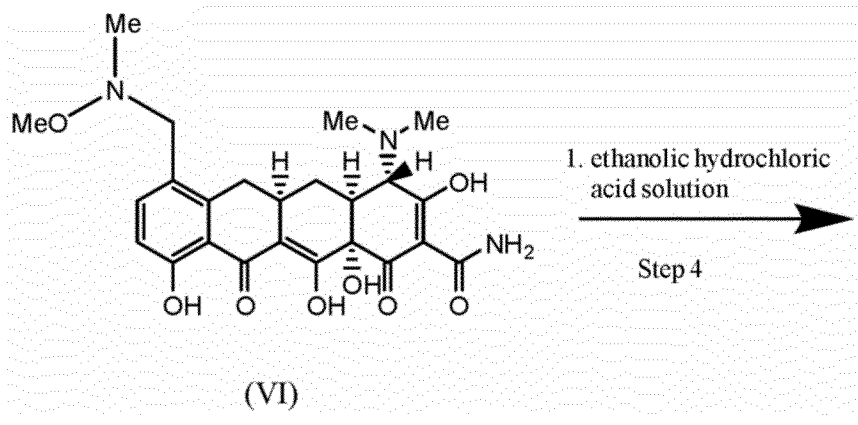

Column 28, Lines 1-14:

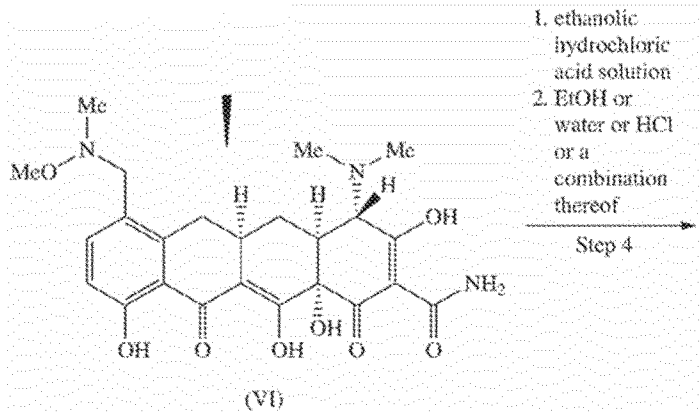

Should read as:

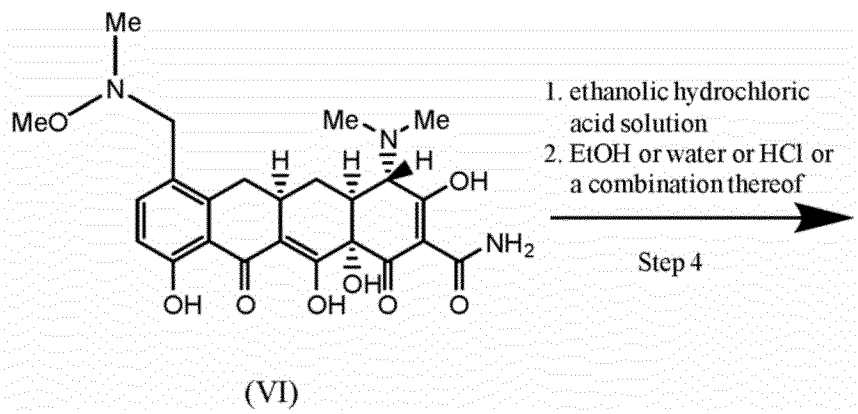
Column 28, Lines 32-42:
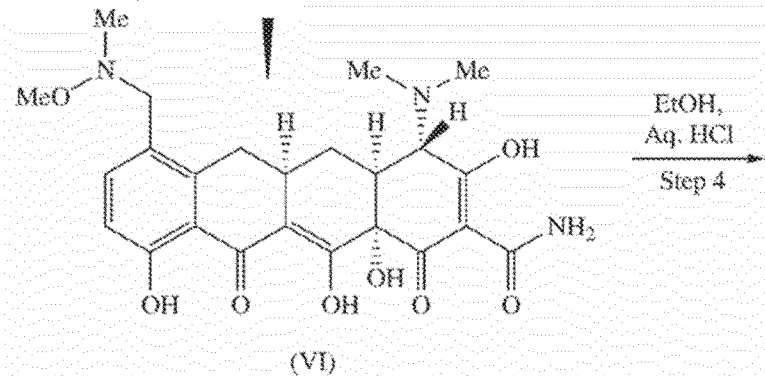
Should read as:
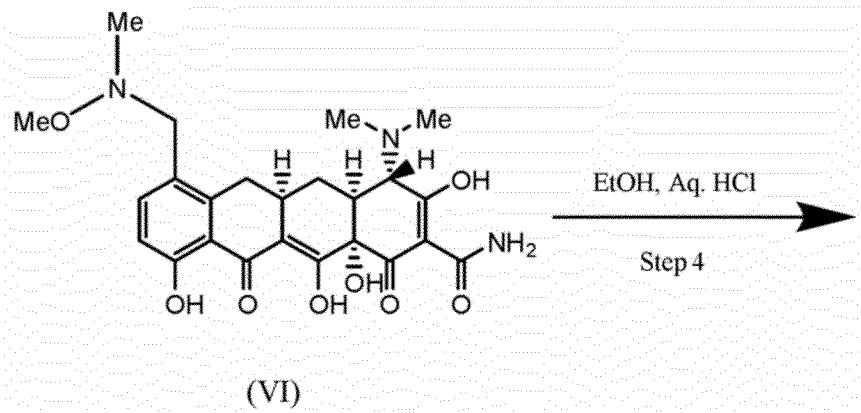
In the Claims
In Claim 1, Column 42, Line 50, after "(iv) acetone", insert -- ; --
In Claim 2, Column 44, Line 1, replace "V." with "v."
In Claim 5, Column 44, Line 11, replace "V." with "v."